(12) United States Patent
Gao et al.

(10) Patent No.: US 7,012,089 B2
(45) Date of Patent: Mar. 14, 2006

(54) [1,4]DIAZOCINO[7,8,1-HI]INDOLE DERIVATIVES AS ANTIPSYCHOTIC AND ANTIOBESITY AGENTS

(75) Inventors: Hong Gao, Belle Mead, NJ (US); Gary P. Stack, Ambler, PA (US); Annmarie L. Sabb, Pennington, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/422,657

(22) Filed: Apr. 24, 2003

(65) Prior Publication Data

US 2004/0034005 A1 Feb. 19, 2004

Related U.S. Application Data

(60) Provisional application No. 60/375,349, filed on Apr. 25, 2002.

(51) Int. Cl.
*C07D 245/04* (2006.01)
*C07D 487/06* (2006.01)
*A61K 31/395* (2006.01)
*A61P 25/18* (2006.01)
*A61P 25/24* (2006.01)

(52) U.S. Cl. .................. 514/410; 514/411; 540/472
(58) Field of Classification Search ............. 540/472; 514/410, 411
See application file for complete search history.

(56) References Cited

U.S. PATENT DOCUMENTS

| | | | |
|---|---|---|---|
| 3,158,619 A | 11/1964 | Wagner | |
| 3,235,564 A | 2/1966 | Wagner et al. | |
| 3,296,252 A | 1/1967 | Frey et al. | |
| 3,329,676 A | 7/1967 | Bell et al. | |
| 3,335,134 A | 8/1967 | Frey et al. | |
| 3,417,101 A | 12/1968 | Bell et al. | |
| 3,466,274 A | 9/1969 | de Ridder | |
| 3,714,149 A | 1/1973 | Hester, Jr. | |
| 3,914,250 A | 10/1975 | Kim | |
| 4,880,814 A | 11/1989 | Chu et al. | |
| 4,997,831 A | 3/1991 | Bays et al. | |
| 5,045,545 A | 9/1991 | Bays et al. | |
| 5,834,454 A | 11/1998 | Kitano et al. | |
| 6,414,144 B1 | 7/2002 | Welmaker et al. | |
| 6,503,900 B1 | 1/2003 | Sabb et al. | |
| 2002/0055504 A1 | 5/2002 | Chan | |
| 2002/0058689 A1 | 5/2002 | Welmaker et al. | |
| 2002/0062022 A1 | 5/2002 | Sabb et al. | |
| 2002/0107242 A1 | 8/2002 | Sabb et al. | |
| 2002/0119966 A1 | 8/2002 | Sabb et al. | |
| 2002/0128261 A1 | 9/2002 | Sabb et al. | |
| 2002/0173503 A1 | 11/2002 | Robichand et al. | |
| 2003/0050300 A1 | 3/2003 | McWhorter, Jr. | |
| 2004/0009970 A1 | 1/2004 | Wyeth | |
| 2004/0019040 A1 | 1/2004 | Wyeth | |

FOREIGN PATENT DOCUMENTS

| | | |
|---|---|---|
| EP | 0 344 015 A2 | 11/1989 |
| EP | 0 357 417 A1 | 3/1990 |
| JP | 02-040379 | 2/1990 |
| JP | 10-237073 | 9/1998 |
| JP | 2001-89461 | 4/2001 |
| SU | 930902 | 11/1982 |
| WO | WO 90/15058 A1 | 12/1990 |
| WO | WO 96/29316 | 9/1996 |
| WO | WO 97/30999 A1 | 8/1997 |
| WO | WO 97/31000 A1 | 8/1997 |
| WO | WO 99/66934 A1 | 12/1999 |
| WO | WO 99/67219 A1 | 12/1999 |
| WO | WO 00/35922 | 6/2000 |
| WO | WO 00/40226 A2 | 7/2000 |
| WO | WO 00/64899 A1 | 11/2000 |
| WO | WO 00/77002 A1 | 12/2000 |
| WO | WO 01/12602 A1 | 2/2001 |
| WO | WO 01/12603 A1 | 2/2001 |
| WO | WO 01/64246 A2 | 9/2001 |
| WO | WO 02/08186 | 1/2002 |
| WO | WO 02/36596 A2 | 5/2002 |
| WO | WO 02/42304 A2 | 5/2002 |
| WO | WO 02/059124 A2 | 8/2002 |
| WO | WO 02/059129 A1 | 8/2002 |

OTHER PUBLICATIONS

Gregory E. Martin et al., J. Med. Chem., 32, 1052–1056 (1989).
J.L. Browning et al., Society for Neuroscience Abstracts, 25(2), 2075, Abstract 830.12, (1999).
Jackson B. Hester et al., J. Med. Chem., 13, 827–835 (1970).
Dong H. Kim, J. Heterocycl. Chem., 13(6), 1187–1192 (1976).
H.P. Haerter et al., Chimia, 30, 50–52 (1976).
Oliver H. Lowry et al., J. Biol. Chem., 193, 265–275 (1951).
Samuel H. Wilen, et al., Tetrahedron, 33, 2725–2736 (1977).
Shunji Naruto et al., Tetrahedron Letters, 39, 3399–3402 (1975).
Giuseppe Digiovanni et al., Synapse, 35, 53–61 (2000).
Vincenzo Dimatteo et al., Neuropharmacology, 37, 265–272 (1998).

(Continued)

*Primary Examiner*—Bruck Kifle
(74) *Attorney, Agent, or Firm*—Kimberly R. Hild

(57) ABSTRACT

Compounds of formula (I) or pharmaceutically acceptable salts thereof are provided:

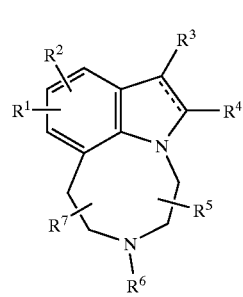

where $R^1$ through $R^7$ are defined herein. The compounds of formula (I) are 5HT2c agonists or partial agonists, and are useful for treating a variety of disorders.

32 Claims, No Drawings

OTHER PUBLICATIONS

Vincenzo Dimatteo, et al., Neuropharmacology, 38, 1195–1205 (1999).
M.J. Millan et al., Neuropharmacology, 37, 953–955 (1998).
Prakash S. Masand, Exp. Opin. Pharmacother, 1(3), 377–389 (2000).
David B. Allison et al., Am. J. Psychiatry, 156(11), 1686–1696 (1999).
P.J. Cowan et al., Human Psychopharmacology, 10, 385–391 (1995).
A. Schotte et al., Psychopharmacology, 124, 57–73 (1996).
Susan H. Fox et al., Experimental Neurology, 151, 35–49 (1998).
R. Whitaker, Spectrum, 2, 1–12 (2000).
Katsunori Nonogaki et al., Nature Medicine, 4(10) 1152–1156 (1998).
Laurence H. Tecott et al., Nature, 374, 542–546 (1995).
P.A. Sargent et al., Psychopharmacology, 133, 309–312 (1997).
M.J. Piesla et al., International Congress on Schizophrenia Research (2001).
Craig D. Applegate et al., Experimental Neurology, 154, 522–530 (1998).
Mark J. Millan et al., European Journal of Pharmacology, 325, 9–12 (1997).
Andrew J. Grottick et al., The Journal of Pharmacology & Experimental Therapeutics, 295(3), 1183–1191 (2000).
Duckhyun Kim et al., Experimental Neurology, 169, 496–500 (2001).
Roger M. Nitsch et al., The Journal of Biological Chemistry, 271(8), 4188–4194 (1996).
J.R. Martin et al., The Journal of Pharmacology & Experimental Therapeutics, 286(2), 913–924 (1998).
Marie–Christine Buhot, Current Opinion in Neurobiology, 7, 243–254 (1997).
Yuhao Li et al., European Journal of Pharmacology, 392, 71–77 (2000).
Jason Bennett et al., www.emedicine.com, "Delusional Disorder" (Apr. 2002).
Sharon Rosenzweig–Lipson et al., "Antipsychotic–like Effects of the 5-$HT_{2c}$ Selective Agonist WAY–163909 in Rodents", Serotonin Symposium–EPHAR, Porto, Portugal, (Jul. 2004).
Michael First, Diagnostic and Statistical Manual of Mental Disorders DSM–IV–TR, Mood Disorders, Introduction, Adjustment Disorders, American Psychiatric Assoc. (2000).
Sharon Rosenzweig–Lipson et al., "Antidepressant–like Effects of the 5-$HT_{2c}$ Selective Agonist WAY–163909 in Rodents", Serotonin Symposium–EPHAR, Porto, Portugal, (Jul. 2004).
Sharon Rosenzweig–Lipson et al., "Pharmacological Characterization of WAY–163909, a Novel 5-$HT_{2c}$ Receptor Selective Agonist", Serotonin Symposium–EPHAR, Porto, Portugal, (Jul. 2004).
A.N. Grinev et al., Chem. Heterocycl. Compd., 19(9), 959–961 (1983).
A.N. Grinev et al., Chem. Heterocycl. Compd., 19(12), 1312–1315 (1983).
E.V. Lamanova et al., Pharm. Chem., J., 23(2), 113–115 (1989).
D.H. Kim et al., Journal of Medicinal Chemistry, 20(2), 209–212 (1977).
D.H. Kim, J. Heterocyclic Chem., 13, 1187–1192 (1976).
L. Toscano et al., J. Heterocyclic Chem., 13, 475–480 (1976).
A. Katritzky et al., Synthesis, 10, 1487–1490 (1998).
F. Gatta et al., Edizione Scientifica, 30(8), 631–641 (1975).
W. Lopes et al., Journal of Brazilian Chemical Society, 4(1), 34–39 (1993).
S. Rosenzweig–Lipson et al., The FASEB Journal, 14, A1321 (2000).

[1,4]DIAZOCINO[7,8,1-HI]INDOLE DERIVATIVES AS ANTIPSYCHOTIC AND ANTIOBESITY AGENTS

CROSS REFERENCE TO RELATED APPLICATIONS

This application claims the benefit under 35 U.S.C. §119 (e) to U.S. provisional application Ser. No. 60/375,349 filed Apr. 25, 2002, which is hereby incorporated by reference in its entirety.

BACKGROUND OF THE INVENTION

Schizophrenia affects approximately 5 million people. At present, the most widespread treatments for schizophrenia are the 'atypical' antipsychotics, which combine dopamine ($D_2$) receptor antagonism with serotonin (5-$HT_{2A}$) receptor antagonism. Despite the reported advances in efficacy and side-effect liability of a typical antipsychotics over typical antipsychotics, these compounds do not adequately treat all of the symptoms of schizophrenia and are accompanied by problematic side effects including weight gain (Allison, D. B., et. al., Am. J. Psychiatry, 156: 1686–1696, 1999; Masand, P. S., Exp. Opin. Pharmacother. I: 377–389, 2000; Whitaker, R., Spectrum Life Sciences. Decision Resources. 2:1–9, 2000). Novel antipsychotics which are effective in treating the mood disorders or the cognitive impairments in schizophrenia without producing weight gain would represent a significant advance in the treatment of schizophrenia.

5-$HT_{2C}$ agonists and partial agonists represent a novel therapeutic approach toward the treatment of schizophrenia. Several lines of evidence support a role for 5-$HT_{2C}$ receptor agonism as a treatment for schizophrenia. Studies with 5-$HT_{2C}$ antagonists suggest that these compounds increase synaptic levels of dopamine and may be effective in animal models of Parkinson's disease (Di Matteo, V., et. al., Neuropharmacology 37: 265–272, 1998; Fox, S. H., et. al., Experimental Neurology 151: 35–49, 1998). Since the positive symptoms of schizophrenia are associated with increased levels of dopamine, compounds with actions opposite those of 5-$HT_{2C}$ antagonists such as 5-$HT_{2C}$ agonists and partial agonists should reduce levels of synaptic dopamine. Recent studies have demonstrated that 5-$HT_{2C}$ agonists decrease levels of dopamine in the prefrontal cortex and nucleus accumbens (Millan, M. J., et. al., Neuropharmacology 37: 953–955, 1998; Di Matteo, V., et. al., Neuropharmacology 38: 1195–1205, 1999; Di Giovanni, G., et. al., Synapse 35: 53–61, 2000), brain regions that are thought to mediate critical antipsychotic effects of drugs like clozapine. In contrast, 5-$HT_{2C}$ agonists do not decrease dopamine levels in the striatum, the brain region most closely associated with extrapyramidal side effects. In addition, a recent study demonstrates that 5-$HT_{2C}$ agonists decrease firing in the ventral tegmental area (VTA), but not in substantia nigra. The differential effects of 5-$HT_{2C}$ agonists in the mesolimbic pathway relative to the nigrostriatal pathway suggests that 5-$HT_{2C}$ agonists will have limbic selectivity and will be less likely to produce extrapyramidal side effects associated with typical antipsychotics.

Atypical antipsychotics bind with high affinity to 5-$HT_{2C}$ receptors and function as 5-$HT_{2C}$ receptor antagonists or inverse agonists. Weight gain is a problematic side effect associated with a typical antipsychotics such as clozapine and olanzapine and it has been suggested that 5-$HT_{2C}$ antagonism is responsible for the increased weight gain. Conversely, stimulation of the 5-$HT_{2C}$ receptor is known to result in decreased food intake and body weight (Walsh et. al., Psychopharmacology 124: 57–73, 1996; Cowen, P. J., et. al., Human Psychopharmacology 10: 385–391, 1995; Rosenzweig-Lipson, S., et. al., ASPET abstract, 2000). As a result, 5-$HT_{2C}$ agonists and partial agonists will be less likely to produce the body weight increases associated with current a typical antipsychotics. Indeed, 5-$HT_{2C}$ agonists and partial agonists are of great interest for the treatment of obesity, a medical disorder characterized by an excess of body fat or adipose tissue and associated with such comorbidities as Type II diabetes, cardiovascular disease, hypertension, hyperlipidemia, stroke, osteoarthritis, sleep apnea, gall bladder disease, gout, some cancers, some infertility, and early mortality. Other therapeutic indications for 5-$HT_{2C}$ agonists and partial agonists include obsessive compulsive disorder, depression (such as depressive disorders and major depressive episodes), panic disorder, sleep disorders, and eating disorders.

SUMMARY OF THE INVENTION

In one embodiment, the present invention provides compounds of formula (I)

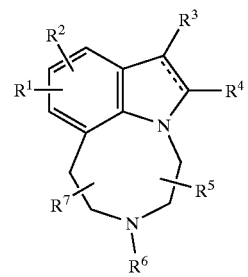

wherein
$R^1$ and $R^2$ are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

$R^3$ and $R^4$ are, independently, hydrogen or alkyl of 1 to 6 carbon atoms, or $R^3$ and $R^4$, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sultone, wherein the cyclic moiety may optionally be substituted with 1 to 3 alkyl moieties of 1 to 6 carbon atoms;

$R^5$, $R^6$ and $R^7$ are, independently, hydrogen or alkyl of 1 to 6 carbon atoms; and a dotted line represents an optional double bond;

or a pharmaceutically acceptable salt thereof.

In another embodiment of the present invention, a method of treating a mammal suffering from a condition selected from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, gastrointestinal disorders, obesity, or a central nervous system deficiency associated with trauma, stroke, or spinal cord injury is provided that includes administering to the mammal at least one compound of formula (I) or a pharmaceutically acceptable salt thereof.

In yet another embodiment of the present invention, a pharmaceutical composition is provided that contains at least one compound of formula (I) and at least one pharmaceutically acceptable carrier or excipient.

DESCRIPTION OF THE INVENTION

In accordance with this invention, there is provided a group of antipsychotic and antiobesity agents of formula I:

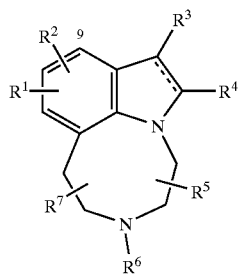

I where
$R^1$ and $R^2$ are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

$R^3$ and $R^4$ are, independently, hydrogen or alkyl of 1 to 6 carbon atoms, or $R^3$ and $R^4$, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sulfone, wherein the cyclic moiety may optionally be substituted with 1 to 3 alkyl moieties of 1 to 6 carbon atoms;

$R^5$, $R^6$ and $R^7$ are, independently, hydrogen or alkyl of 1 to 6 carbon atoms; and a dotted line represents an optional double bond;
or a pharmaceutically acceptable salt thereof.

$R^1$ is preferably hydrogen, halo, cyano, trifluoromethyl, alkyl of 1 to 6 carbon atoms, alkoxy of 1 to 6 carbon atoms, alkanoyl of 2 to 6 carbon atoms or alkanesulfonyl of 1 to 6 carbon atoms. More preferably, $R^1$ is hydrogen, halo, trifluoromethyl or alkyl of 1 to 3 carbon atoms. In still more preferred embodiments of the present invention, $R^1$ is substituted at the 9-position of the [1,4]diazocino[7,8,1-hi] indole as shown above, or for the tetracyclic analoques, where $R^3$ and $R^4$ together form a cyclic moiety, $R^1$ is substituted at the 8-position.

$R^2$ is preferably hydrogen, halo, cyano, trifluoromethyl, alkyl of 1 to 6 carbon atoms, alkoxy of 1 to 6 carbon atoms, alkanoyl of 2 to 6 carbon atoms or alkanesulfonyl of 1 to 6 carbon atoms. More preferably, $R^2$ is hydrogen, halo, trifluoromethyl or alkyl of 1 to 3 carbon atoms.

$R^3$ and $R^4$ are preferably taken together with the carbon atoms to which they are attached to form a cyclic moiety selected from a cycloalkane of 5 to 8 carbon atoms optionally substituted with 1 to 3 alkyl moieties of 1 to 3 carbon atoms, cycloalkene of 5 to 8 carbon atoms, optionally substituted with 1 to 3 alkyl moieties of 1 to 3 carbon atoms, pyran or thiopyran, in which the sulfur atom is optionally oxidized to a sulfoxide or sulfone. More preferably, $R^3$ and $R^4$ are taken together with the carbon atoms to which they are attached to form cycloalkane of 5 to 8 carbon atoms, cycloalkene of 5 to 8 carbon atoms or thiopyran. In still more preferred embodiments of the present invention, $R^3$ and $R^4$ are taken together with the carbon atoms to which they are attached to form cyclopentane, cyclohexane or cyclohexene.

$R^5$ is preferably hydrogen or alkyl of 1 to 3 carbon atoms and more preferably hydrogen.

$R^6$ is preferably hydrogen or alkyl of 1 to 3 carbon atoms and more preferably hydrogen.

$R^7$ is preferably hydrogen or alkyl of 1 to 3 carbon atoms and more preferably hydrogen.

In still other preferred embodiments of the invention, $R^1$ and $R^2$ are independently selected from hydrogen, halo, trifluoromethyl or alkyl of 1 to 3 carbon atoms, $R^5$, $R^6$ and $R^7$ are each hydrogen and $R^3$ and $R^4$, taken together with the carbon atoms to which they are attached, form cyclopentane, cyclohexane or cyclohexene.

Certain of the compounds of this invention contain asymmetric carbon atoms and thus give rise to stereoisomers, including enantiomers and diastereomers. This invention relates to all of the stereoisomers of the [1,4]diazocino[7,8,1-hi]indole derivatives, as well as to mixtures of the stereoisomers. Throughout this application, the name of the product of this invention, where the absolute configuration of an asymmetric center is not indicated, is intended to embrace the individual stereoisomers as well as mixtures of stereoisomers.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl, as used herein, refers to an aliphatic hydrocarbon chain and includes, but is not limited to, straight and branched chains such as methyl, ethyl, n-propyl, isopropyl, n-butyl, isobutyl, sec-butyl, t-butyl, n-pentyl, isopentyl, neopentyl, n-hexyl, and isohexyl. Lower alkyl refers to alkyl having 1 to 3 carbon atoms.

Alkanamido, as used herein, refers to the group R—C(=O)—NH— where R is an alkyl group of 1 to 5 carbon atoms.

Alkanoyl, as used herein, refers to the group R—C(=O)— where R is an alkyl group of 1 to 5 carbon atoms.

Alkanoyloxy, as used herein, refers to the group R—C(=O)—O— where R is an alkyl group of 1 to 5 carbon atoms.

Alkanesulfonamido, as used herein, refers to the group R—S(O)$_2$—NH— where R is an alkyl group of 1 to 6 carbon atoms.

Alkanesulfonyl, as used herein, refers to the group R—S(O)$_2$— where R is an alkyl group of 1 to 6 carbon atoms.

Alkoxy, as used herein, refers to the group R—O— where R is an alkyl group of 1 to 6 carbon atoms.

Carboxamido, as used herein, refers to the group NH$_2$—C(=O)—.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts, including mono- and bi-salts, are those derived from such organic and inorganic acids such as, but not limited to acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:
3-Methyl-2,3,4,5,10,11-hexahydro-1H,9H-cyclopenta[b][1,4]diazocino[7,8,1-hi]indole;
2,3,4,5,10,11-Hexahydro-1H,9H-cyclopenta[b][1,4]diazocino[7,8,1-hi]indole;
3-Methyl-2,3,4,5,9,10,11,11a-octahydro-1H,8bH-cyclopenta[b][1,4]diazocino[7,8,1-hi]indole;
2,3,4,5,9,10,11,11a-Octahydro-1H,8bH-cyclopenta[b][1,4]diazocino[7,8,1-hi]indole;
3-Methyl-2,3,4,5,9,10,11,12-octahydro-1H-[1,4]diazocino[7,8,1-jk]carbazole;
2,3,4,5,9,10,11,12-Octahydro-1H-[1,4]diazocino[7,8,1-jk]carbazole;
3-Methyl-2,3,4,5,8b,9,10,11,12,12a-decahydro-1H-[1,4]diazocino[7,8,1-jk]carbazole;
2,3,4,5,8b,9,10,11,12,12a-Decahydro-1H-[1,4]diazocino[7,8,1-jk]carbazole;
3-Methyl-2,3,4,5,10,11,12,13-octahydro-1H,9H-cyclohepta[b][1,4]diazocino[7,8,1-hi]indole;
2,3,4,5,10,11,12,13-Octahydro-1H,9H-cyclohepta[b][1,4]diazocino[7,8,1-hi]indole;
3-Methyl-2,3,4,5,11,12-hexahydro-1H,9H-[1,4]diazocino[7,8,1-hi]thiopyrano[4,3-b]indole;
6-Chloro-3-methyl-2,3,4,5,10,11-hexahydro-1H,9H-cyclopenta[b][1,4]diazocino[7,8,1-hi]indole;
6-Chloro-3-methyl-2,3,4,5,9,10,11,12-octahydro-1H-[1,4]diazocino[7,8,1-jk]carbazole;
6-Chloro-3-methyl-2,3,4,5,10,11,12,13-octahydro-1H,9H-cyclohepta[b][1,4]diazocino[7,8,1-hi]indole;
6-Chloro-3-Methyl-2,3,4,5,9,10,11,11a-octahydro-1H,8bH-cyclopenta[b][1,4]diazocino[7,8,1-hi]indole;
6-Chloro-3-methyl-2,3,4,5,9,10,11,12,13,13a-decahydro-1H,8bH-cyclohepta[b][1,4]diazocino[7,8,1-hi]indole;
6-Chloro-2,3,4,5,10,11-hexahydro-1H,9H-cyclopenta[b][1,4]diazocino[7,8,1-hi]indole;
6-Chloro-2,3,4,5,9,10,11,12-octahydro-1H-[1,4]diazocino[7,8,1-jk]carbazole;
6-Chloro-2,3,4,5,10,11,12,13-octahydro-1H,9H-cyclohepta[b][1,4]diazocino[7,8,1-hi]indole;
6-Chloro-2,3,4,5,9,10,11,11a-octahydro-1H,8bH-cyclopenta[b][1,4]diazocino[7,8,1-hi]indole;
6-Chloro-3-ethyl-2,3,4,5,9,10,11,11a-octahydro-1H,8bH-cyclopenta[b][1,4]diazocino[7,8,1-hi]indole;
6-Chloro-2,3,4,5,9,10,11,12,13,13a-decahydro-1H,8bH-cyclohepta[b][1,4]diazocino[7,8,1-hi]indole;
6-Chloro-3-ethyl-2,3,4,5,8b,9,10,11,12,12a-decahydro-1H-[1,4]diazocino[7,8,1-jk]carbazole;
8-Fluoro-3-methyl-2,3,4,5,10,11-hexahydro-1H,9H-cyclopenta[b][1,4]diazocino[7,8,1-hi]indole;
8-Fluoro-3-methyl-2,3,4,5,9,10,11,12-octahydro-1H-[1,4]diazocino[7,8,1-jk]carbazole;
8-Fluoro-3-methyl-2,3,4,5,9,10,11,11a-octahydro-1H,8bH-cyclopenta[b][1,4]diazocino[7,8,1-hi]indole;
8-Fluoro-3-methyl-2,3,4,5,8b,9,10,11,12,12a-decahydro-1H-[1,4]diazocino[7,8,1-jk]carbazole;
8-Fluoro-2,3,4,5,10,11-hexahydro-1H,9H-cyclopenta[b][1,4]diazocino[7,8,1-hi]indole;
8-Fluoro-2,3,4,5,9,10,11,12-octahydro-1H-[1,4]diazocino[7,8,1-jk]carbazole;
8-Fluoro-2,3,4,5,9,10,11,11a-octahydro-1H,8bH-cyclopenta[b][1,4]diazocino[7,8,1-hi]indole;
8-Fluoro-2,3,4,5,8b,9,10,11,12,12a-decahydro-1H-[1,4]diazocino[7,8,1-jk]carbazole;
(+)-(8bR*,12aR*)-8-Fluoro-2,3,4,5,8b,9,10,11,12,12a-decahydro-1H-[1,4]diazocino[7,8,1-jk]carbazole;
(−)-(8bR*,12aR*)-8-Fluoro-2,3,4,5,8b,9,10,11,12,12a-decahydro-1H-[1,4]diazocino[7,8,1jk]carbazole;
8-Chloro-3-methyl-2,3,4,5,10,11-hexahydro-1H,9H-cyclopenta[b][1,4]diazocino[7,8,1-hi]indole;
8-Chloro-3-methyl-2,3,4,5,9,10,11,12-octahydro-1H-[1,4]diazocino[7,8,1-jk]carbazole;
8-Chloro-3-methyl-2,3,4,5,9,10,11,11a-octahydro-1H,8bH-cyclopenta[b][1,4]diazocino[7,8,1-hi]indole;
8-Chloro-3-methyl-2,3,4,5,8b,9,10,11,12,12a-decahydro-1H-[1,4]diazocino[7,8,1-jk]carbazole;
8-Chloro-2,3,4,5,10,11-hexahydro-1H,9H-cyclopenta[b][1,4]diazocino[7,8,1-hi]indole;
8-Chloro-2,3,4,5,9,10,11,12-octahydro-1H-[1,4]diazocino[7,8,1-jk]carbazole;
8-Chloro-2,3,4,5,9,10,11,11a-octahydro-1H,8bH-cyclopenta[b][1,4]diazocino[7,8,1-hi]indole;
8-Chloro-2,3,4,5,8b,9,10,11,12,12a-decahydro-1H-[1,4]diazocino[7,8,1-jk]carbazole;
(+)-(8bR*,12aR*)-8-Chloro-2,3,4,5,8b,9,10,11,12,12a-decahydro-1H-[1,4]diazocino[7,8,1-jk]carbazole;
(−)-(8bR*,2aR*)-8-Chloro-2,3,4,5,8b,9,10,11,12,12a-decahydro-1H-[1,4]diazocino[7,8,1-jk]carbazole;
3-Methyl-2,3,4,5,9,10,11,12-octahydro-1H,9H-[1,4]diazocino[7,8,1-hi]thiopyrano[4,3-b]indole;
(+)-(8bR*,11aR*)-2,3,4,5,9,10,11,11a-Octahydro-1H,8bH-cyclopenta[b][1,4]diazocino[7,8,1-hi]indole;
(−)-(8bR*,11aR*)-2,3,4,5,9,10,11,11a-Octahydro-1H,8bH-cyclopenta[b][1,4]diazocino[7,8,1-hi]indole;
(+)-(8bR*,12aR*)-2,3,4,5,8b,9,10,11,12,12a-Decahydro-1H-[1,4]diazocino[7,8,1-jk]carbazole;
(−)-(8bR*,12aR*)-2,3,4,5,8b,9,10,11,12,12a-Decahydro-1H-[1,4]diazocino[7,8,1-jk]carbazole;
and pharmaceutically acceptable salts thereof.

The [1,4]diazocino[7,8,1-hi]indole derivatives of the present invention are prepared as illustrated in scheme I. Variables used are as defined for Formula I, unless otherwise noted. The appropriately substituted 3,4,5,6-tetrahydro-1H- benzo[e][1,4]diazocin-2-one (1), in which $R^6$ is alkyl, is reduced to the 1,2,3,4,5,6-hexahydro-benzo[e][1,4]diazocine (2) with a suitable reducing agent such as lithium aluminum hydride or borane-THF in a solvent such as ether or tetrahydrofuran. The resulting secondary amine is nitrosated with sodium nitrite in aqueous hydrochloric acid to give the nitrosamine (3), which is subsequently reduced to a hydrazine (4) with a suitable reducing agent such as lithium aluminum hydride or zinc in acetic acid. The hydrazine (4) is caused to undergo a Fischer indole synthesis by treatment with appropriately substituted ketone or aldehyde and an acid such as p-toluenesulfonic acid in a solvent such as n-propanol to give the compounds of the invention (Ia) in which $R^6$ is alkyl and the optional double bond is present. Compounds of the invention in which $R^6$ is hydrogen (Ib) may be produced from the Fischer indole product (Ia) by treatment with an appropriate dealkylating agent such as 1-chloroethyl chloroformate in a solvent such as refluxing 1,2-dichloroethane, followed by a period of reflux in methanol. Further treatment with a suitable reducing agent such as sodium cyanoborohydride in an acid medium such as acetic acid gives the compounds of the invention (Ic) in which the optional double bond is absent. Compounds of the invention in which $R^6$ is alkyl and the optional double bond is absent (Id) may be prepared either by reduction of the Fischer indole product (Ia) directly with sodium cyanoborohydride in acetic acid or alternatively by alkylation of Ic with the appropriate alkyl halide or tosylate in the presence of a suitable base such as sodium carbonate or a tertiary amine in a solvent such as dimethyl formamide.

Scheme I

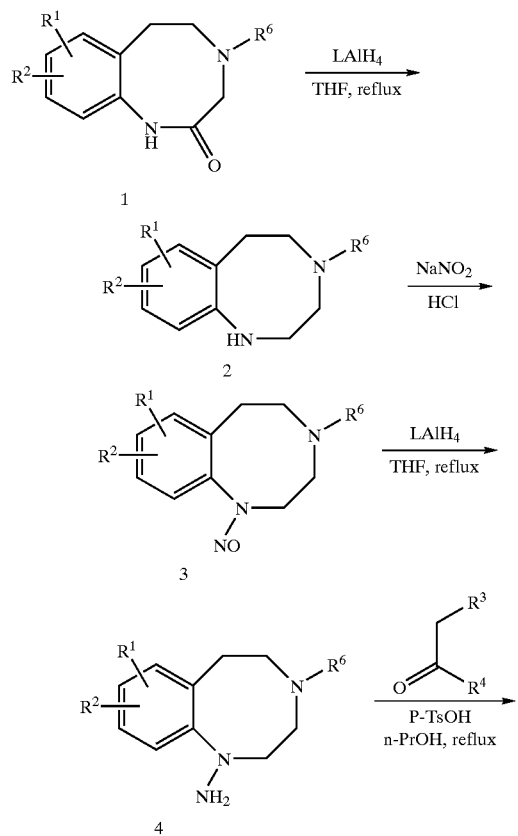

The substituted 3,4,5,6-tetrahydro-1H-benzo[e][1,4]diazocin-2-ones appropriate for the synthesis of the compounds of this invention are known compounds or can readily be prepared by one schooled in the art using, for example, the sequence illustrated in Scheme 2. The appropriately substituted nitrotoluene (5) is treated with paraformaldehyde in the presence of a suitable base such a potassium hydroxide in a solvent such as DMSO-ethanol to give the phenylethanol (6), which is converted to the bromide (7) using standard procedures, such as treatment with carbon tetrabromide and triphenylphosphine in methylene chloride. The bromide is converted to the phenethylamine (8) by treatment with the appropriate alkylamine at elevated temperature in a high pressure vessel and the phenethylamine alkylated with ethyl bromoacetate in the presence of a base such as potassium carbonate in a suitable solvent such as acetonitrile or dimethylformamide. The resulting amino ester (9) is hydrolyzed to the acid by treatment with hydrobromic acid to give the amino acid (10). Following reduction of the aromatic nitro group with hydrogen in the presence of a suitable catalyst such as platinum on sulfided carbon or palladium on carbon, cyclization to the required 3,4,5,6-tetrahydro-1H-benzo[e][1,4]diazocin-2-one (1) is effected by treatment with a coupling reagent such as dicyclohexylcarbodiimide in a solvent such as pyridine.

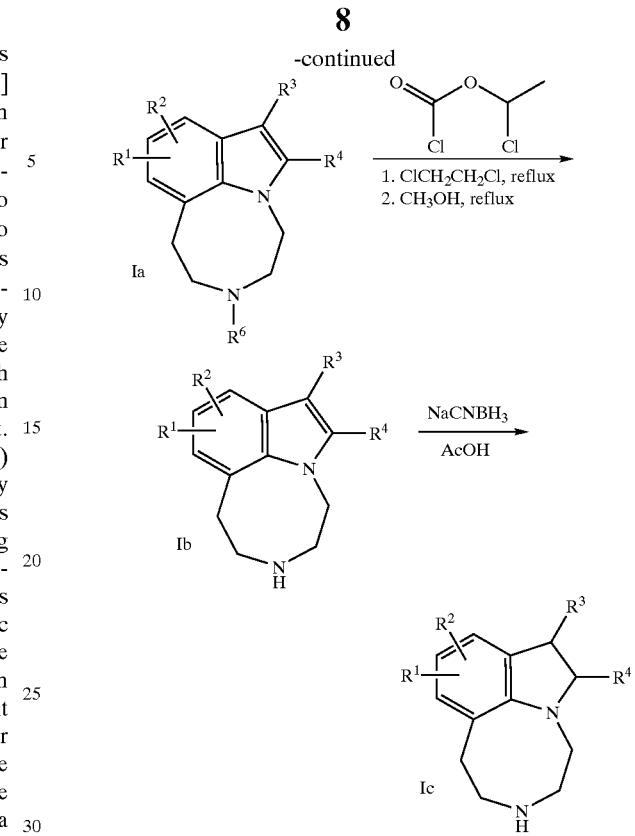

Scheme 2

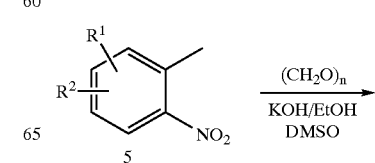

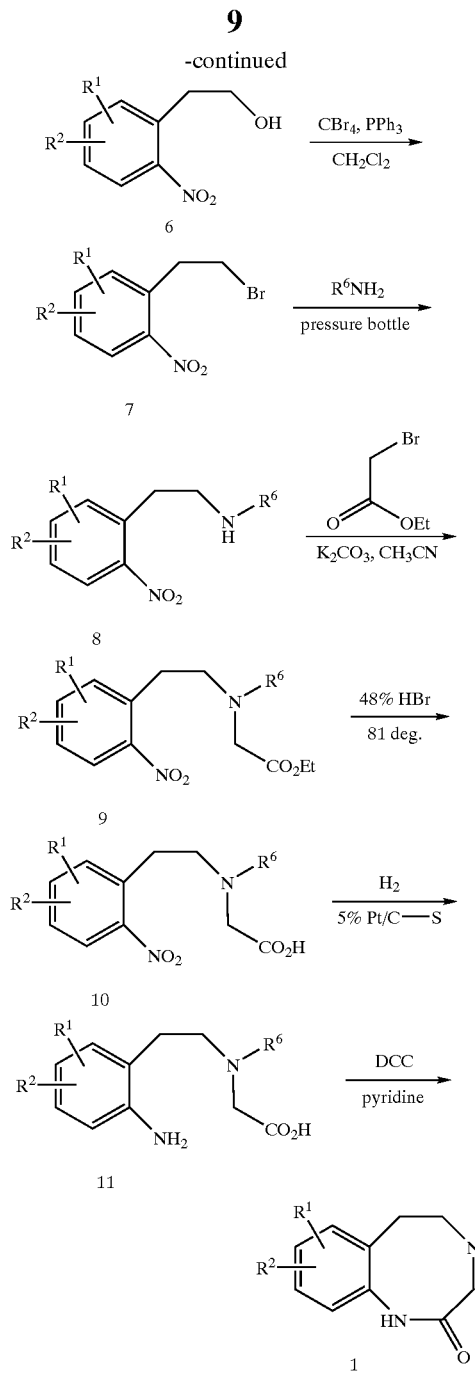

The compounds of this invention are agonists and partial agonists at the 2c subtype of brain serotonin receptors and are thus of interest for the treatment of mental disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorder with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders such as depressive disorders or bipolar disorders often accompany psychotic disorders such as schizophrenia. A more complete description of the aforementioned mental disorders can be found in the Diagnostic and Statistical Manual of Mental Disorders, 4$^{th}$ edition, Washington, D.C., American Psychiatric Association (1994).

The compounds of the present invention are also of interest for the treatment of epilepsy; migraines; sexual dysfunction; sleep disorders; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality. The compounds of the present invention can also be used to treat central nervous system deficiencies associated, for example, with trauma, stroke, and spinal cord injuries. The compounds of the present invention can therefore be used to improve or inhibit further degradation of central nervous system activity during or following the malady or trauma in question. Included in these improvements are maintenance or improvement in motor and motility skills, control, coordination and strength.

The ability of the compounds of this invention to act as 5HT$_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

To evaluate high affinity for the 5HT$_{2C}$ receptor, a CHO (Chinese Hamster Ovary) cell line transfected with the cDNA expressing the human 5-hydroxytryptamine-2C (h-5-HT$_{2C}$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10–25 microliter (µl) volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1–2 mg per ml of suspension. The preparation membrane suspension (many times concentrated) was aliquoted in 1 ml volumes and stored at −70° C. until used in subsequent binding experiments.

Binding measurements were performed in a 96 well microtiter plate format, in a total volume of 200 μl. To each well was added: 60 μl of incubation buffer made in 50 mM Tris.HCl buffer, pH 7.4 and containing 4 mM $CaCl_2$; 20 μl of [$^{125}$I] DOI (S.A., 2200 Ci/mmol, NEN Life Science).

The dissociation constant, KD of [$^{125}$I] DOI at the human serotonin $5HT_{2C}$ receptor was 0.4 nM by saturation binding with increasing concentrations of [$^{125}$I] DOI. The reaction was initiated by the final addition of 100.0 μl of tissue suspension containing 50 μg of receptor protein. Nonspecific binding is measured in the presence of 1 μM unlabeled DOI added in 20.0 μl volume. Test compounds were added in 20.0 ml. The mixture was incubated at room temperature for 60 min. The incubation was stopped by rapid filtration. The bound ligand-receptor complex was filtered off on a 96 well unifilter with a Packard.®Filtermate 196 Harvester. The bound complex caught on the filter disk was dried in a vacuum oven heated to 60° C. and the radioactivity measured by liquid scintillation with 40 μl Microscint-20 scintillant in a Packard TopCount® equipped with six (6) photomultiplier detectors.

Specific binding is defined as the total radioactivity bound less the amount bound in the presence of 1 μM unlabeled DOI. Binding in the presence of varying concentrations of test drugs is expressed as percent of specific binding in the absence of drug. These results are then plotted as log % bound vs log concentration of test drug. Non linear regression analysis of data points yields both the $IC_{50}$ and the $K_i$ values of test compounds with 95% confidence limits. Alternatively, a linear regression line of decline of data points is plotted, from which the $IC_{50}$ value can be read off the curve and the $K_i$ value determined by solving the following equation:

$$K_i = \frac{IC_{50}}{1 + L/KD}$$

where L is the concentration of the radioactive ligand used and the KD is the dissociation constant of the ligand for the receptor, both expressed in nM.

The following $K_i$'s (95% confidence interval) are provided for various reference compounds:

| | |
|---|---|
| Ritanserin | 2.0 (1.3–3.1) nM |
| Ketanserin | 94.8 (70.7–127.0) nM |
| Mianserin | 2.7 (1.9–3.8) nM |
| Clozapine | 23.2 (16.0–34.0) nM |
| Methiothepin | 4.6 (4.0–6.0) nM |
| Methysergide | 6.3 (4.6–8.6) nM |
| Loxapine | 33.0 (24.0–47.0) nM |
| mCPP | 6.5 (4.8–9.0) nM |
| DOI | 6.2 (4.9–8.0) nM |

The ability of the compounds of the invention to produce an agonist response at brain $5\text{-}HT_{2C}$ was assessed by determining their effect on calcium mobilization using the following procedure: CHO cells stably expressing the human $5\text{-}HT_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hours prior to the evaluation of $5\text{-}HT_{2C}$ receptor-stimulated calcium mobilization. For calcium studies cells were loaded with the calcium indicator dye Fluo-3-AM in Hank's buffered saline (HBS) for 60 minutes at 37° C. Cells were washed with HBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510–560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology the calcium changes in response to different concentrations of agonist were determined using a maximum minus minimum calculation of the raw fluorescence count data. Calcium changes were then expressed as a percentage of the response observed with a maximally effective concentration of 5-HT and $EC_{50}$ values were estimated by non-linear regression analysis of the log-concentration % maximum 5-HT response curves using the 4-parameter logistic function.

The following $EC_{50}$'s and $IC_{50}$'s are provided for various reference compounds:

5-HT $EC_{50}$ 0.5 nM

DOI $EC_{50}$ 0.5 nM mCPP $EC_{50}$ 5.4 nM

The results of the standard experimental test procedures described in the preceding paragraphs were as follows:

| | $5\text{-}HT_{2c}$ | $5\text{-}HT_{2c}$ Function | |
|---|---|---|---|
| Compound | Affinity KI (nM) | $EC_{50}$ (nM) | Emax (%) |
| Example 1 | 35 | 48 | 45 |
| Example 2 | 38 | 20 | 80 |
| Example 3 | 41 | 37 | 50 |
| Example 4 | 31 | 18 | 90 |
| Example 5 | 10 | 68 | 50 |
| Example 6 | 4 | 6 | 80 |
| Example 7 | 24 | 74 | 60 |
| Example 8 | 22 | 18 | 80 |
| Example 9 | 19 | 275 | 25 |
| Example 10 | 38 | 156 | 90 |
| Example 11 | 38 | | |
| Example 12 | 250 | | |
| Example 13 | 34 | | |
| Example 14 | 250 | | |
| Example 15 | 131 | | |
| Example 16 | 84 | | |
| Example 17 | 156 | | |
| Example 18 | 83 | | |
| Example 19 | 4966 | | |
| Example 20 | 111 | | |
| Example 21 | 137 | | |
| Example 22 | 50 | 326 | 60 |
| Example 23 | 116 | | |
| Example 24 | 93 | | |
| Example 25 | 68 | | |
| Example 26 | 176 | | |
| Example 27 | 13 | 261 | 70 |
| Example 28 | 12 | 36 | 80 |
| Example 29 | 1 | 8 | 90 |
| Example 30 | 16 | 36 | 90 |
| Example 31 | 8 | 87 | 60 |
| Example 32 | 2 | | |
| Example 33 | 1.4 | | |

-continued

| Compound | 5-HT$_{2c}$ Affinity KI (nM) | 5-HT$_{2c}$ Function EC$_{50}$ (nM) | 5-HT$_{2c}$ Function Emax (%) |
| --- | --- | --- | --- |
| Example 34 | 15 | 81 | 40 |
| Example 35 | 11 | 287 | 50 |
| Example 36 | 12 | 467 | 40 |
| Example 37 | 11.6 | 655 | 70 |
| Example 38 | 9.3 | 87 | 90 |
| Example 39 | 2 | 48 | 80 |
| Example 40 | 20 | 81 | 80 |
| Example 41 | 7.5 | 91 | 90 |
| Example 42 | 5.1 | | |
| Example 43 | 7.0 | | |
| Example 44 | 1720 | | |
| Example 45 | 362 | | |
| Example 46 | 19 | 38 | 70 |
| Example 47 | 135 | | |
| Example 48 | 17 | 42 | 70 |

The compounds of this invention thus have affinity for and agonist or partial agonist activity at brain serotonin receptors. They are therefore of interest for the treatment of such CNS disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorder with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders or episodes, such as depressive disorders or episodes often accompany psychotic disorders such as schizophrenia. A more complete description of the aforementioned mental disorders can be found in the Diagnostic and Statistical Manual of Mental Disorders, 4$^{th}$ edition, Washington, D.C., American Psychiatric Association (1994).

The compounds of the present invention are also of interest for the treatment of epilepsy; migraines; sexual dysfunction; sleep disorders; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality. The compounds of the present invention can also be used to treat central nervous system deficiencies associated, for example, with trauma, stroke, spinal cord injuries. The compounds of the present invention can therefore be used to improve or inhibit further degradation of central nervous system activity during or following the malady or trauma in question. Included in these improvements are maintenance or improvement in motor and motility skills, control, coordination and strength.

Thus the present invention provides methods of treating each of the maladies listed above in a mammal, preferably in a human, the methods comprising providing a therapeutically effective amount of a compound of this invention to the mammal in need thereof. By "treating", as used herein, it is meant partially or completely alleviating, inhibiting, preventing, ameliorating and/or relieving the disorder. For example, "treating" as used herein includes partially or completely alleviating, inhibiting or relieving the condition in question. "Mammals" as used herein refers to warm blooded vertebrate animals, such as humans.

Also encompassed by the present invention are pharmaceutical compositions for treating or controlling disease states or conditions of the central nervous system comprising at least one compound of Formula I, mixtures thereof, and/or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be administered by, for example, intramuscular, intraperitoneal or subcutaneous injection. Sterile solutions can also be administered intravenously. Oral administration may be either liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug derivative or analog which will form an equivalent amount of the active compound or substance within the body.

The present invention includes prodrugs of compounds of Formula I. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Delivery Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

Intermediate 1

4-Methyl-3,4,5,6-tetrahydro-2H-benzo[e][1,4]diazocin-1-ylamine

To a solution of 4-methyl-1,2,3,4,5,6-hexahydro-benzo[e][1,4]diazocine (1.2 g, 6.8 mmole) in hydrochloric acid (2 N, 30 mL) cooled to 0° C. was added sodium nitrite (0.9 g, 13 mmole) in water (5 mL). The mixture was stirred for 1 hour at 0° C. and then neutralized with solid sodium bicarbonate and extracted with ethyl acetate (3×100 mL). The combined organic layers were washed with saturated aqueous sodium chloride (200 mL), dried and concentrated to a light brown oil. This oil was redissolved in THF (50 mL) and added to a suspension of lithium aluminum hydride (1.0 g, 25 mmole) in THF (50 mL) and the mixture refluxed for 3 hours under nitrogen. The excess hydride was destroyed at 0° C. by the cautious addition of water. The mixture was diluted with THF (200 mL) and filtered. Evaporation of the filtrate in vacuo provided 1.4 g of the title compound as a light yellow oil.

EXAMPLE 1

3-Methyl-2,3,4,5,10,11-hexahydro-1H,9H-cyclopenta[b][1,4]diazocino[7,8,1-hi]indole To a solution of 4-methyl-3,4,5,6-tetrahydro-2H-benzo[e][1,4]diazocin-1-ylamine (1.55 g, 8.1 mmole) in 1-propanol (100 mL) was added cyclopentanone (5.23 g, 62.3 mmole), followed by p-toluenesulfonic acid monohydrate (3.2 g, 16.8 mmole), and the resulting reaction mixture was refluxed for 40 hours. The reaction mixture was cooled to room temperature and solvent removed in vacuo to produce a brown residue. The residue was diluted with ethyl acetate (300 mL) and washed with saturated aqueous sodium bicarbonate (150 mL), saturated aqueous sodium chloride (150 mL), dried (sodium sulfate) and concentrated in vacuo. Purification by flash column chromatography (silica gel, ethyl acetate:hexanes 1:1) provided 0.50 g of the title compound as a white solid, mp 128–130° C. MS (ESI) m/z 241 ([M+H]+).

Elemental Analysis for: $C_{16}H_{20}N_2.0.04\ CH_2Cl_2$ Calc'd: C, 79.04; H, 8.30; N, 11.49. Found: C, 79.16; H, 8.43; N, 11.30.

EXAMPLE 2

2,3,4,5,10,11-Hexahydro-1H,9H-cyclopenta[b][1,4]diazocino[7,8,1-hi]indole

To a solution of 3-methyl-2,3,4,5,10,11-hexahydro-1H,9H-cyclopenta[b][1,4]diazocino[7,8,1-hi]indole (90 mg, 0.36 mmole) in dichloroethane (10 mL) was added 1-chloroethyl chloroformate (0.15 mL, 1.3 mmole) and the solution refluxed for 24 hours under nitrogen. The reaction mixture was cooled to room temperature and the solvent removed in vacuo and replaced with methanol (25 mL) and refluxed for another 3 hours under nitrogen. The solvent was removed in vacuo and the residue purified by flash column chromatography (silica gel, 1.5% methanol in dichloromethane) to provide 27 mg of the title compound as a light yellow oil. The oil was further treated with one equivalent of fumaric acid in ethanol to form a fumarate salt, mp 180–183° C., which contained a slight excess of fumaric acid. MS (ESI) m/z 227 ([M+H]+).

Elemental Analysis for: $C_{15}H_{18}N_2 \cdot 1.18\ C_4H_4O_4$ Calc'd: C, 65.20; H, 6.30; N, 7.71. Found: C, 65.19; H, 6.61; N, 7.72.

EXAMPLE 3

3-Methyl-2,3,4,5,9,10,11,11a-octahydro-1H,8bH-cyclopenta[b][1,4]diazocino[7,8,1-hi]indole To a solution of 3-methyl-2,3,4,5,10,11-hexahydro-1H,9H-cyclopenta[b][1,4]diazocino[7,8,1-hi]indole (0.40 g, 1.7 mmole) in acetic acid (50 mL) was added sodium cyanoborohydride (95 wt. %, 0.21 g, 3.2 mmole) and the reaction mixture was stirred at room temperature for 1 hour. The solvent was removed in vacuo and the residue was diluted with ethyl acetate (300 mL) and washed with saturated aqueous sodium bicarbonate (150 mL) and saturated aqueous sodium chloride (150 mL), dried (sodium sulfate) and concentrated in vacuo. Purification by flash column chromatography (silica gel, ethyl acetate:hexanes 3:2) provided 0.40 g of the title compound as a light oil. 60 mg of this oil was treated with one equivalent of fumaric acid in ethanol to form a fumarate salt, mp 159–161° C. MS (ESI) m/z 243 ([M+H]+).

Elemental Analysis for: $C_{16}H_{22}N_2 \cdot 1.08\ C_4H_4O_4$ Calc'd: C, 66.37; H, 7.21; N, 7.62. Found: C, 66.26; H, 7.38; N, 7.50.

EXAMPLE 4

2,3,4,5,9,10,11,11a-Octahydro-1H,8bH-cyclopenta[b][1,4]diazocino[7,8,1-hi]indole To a solution of 3-methyl-2,3,4,5,9,10,11,11a-octahydro-1H,8bH-cyclopenta[b][1,4]diazocino[7,8,1-hi]indole (0.40 g, 1.6 mmole) in dichloroethane (80 mL) was added 1-chloroethyl chloroformate (1.2 mL, 10.8 mmole) and the solution refluxed for 24 hours under nitrogen. The reaction mixture was cooled to room temperature and the solvent removed in vacuo and replaced with methanol (200 mL) and refluxed for another 3 hours under nitrogen. The solvent was removed in vacuo and the residue purified by flash column chromatography (silica gel, 1.5% methanol in dichloromethane) to provide 0.27 g of the title compound as an off-white solid. A THF solution of this compound was further treated with hydrogen chloride to provide 0.22 g of a hydrochloride salt, mp 137–140° C. MS (ESI) m/z 229 ([M+H]+).

Elemental Analysis for: $C_{15}H_{20}N_2 \cdot 2\ HCl \cdot H_2O$ Calc'd: C, 56.43; H, 7.58; N, 8.77. Found: C, 56.68; H, 7.82; N, 8.50.

EXAMPLE 5

3-Methyl-2,3,4,5,9,10,11,12-octahydro-1H-[1,4diazocino[7,8,1-jk]carbazole

To a solution of 4-methyl-3,4,5,6-tetrahydro-2H-benzo[e][1,4]diazocin-1-ylamine (1.55 g, 8.1 mmole) in 1-propanol (100 mL) was added cyclohexanone (4.73 g, 48.0 mmole), followed by p-toluenesulfonic acid monohydrate (3.2 g, 16.8 mmole), and the resulting reaction mixture was refluxed for 40 hours. The reaction mixture was cooled to room temperature and solvent removed in vacuo to produce a brown residue. The residue was diluted with ethyl acetate (300 mL) and washed with saturated aqueous sodium bicarbonate (150 mL), saturated aqueous sodium chloride (150 mL), dried (sodium sulfate) and concentrated in vacuo. Purification by flash column chromatography (silica gel, ethyl acetate:hexanes 1:1) provided 1.2 g of the title compound as a white solid, mp 129–131° C. MS (ESI) m/z 255 ([M+H]+).

Elemental Analysis for: $C_{17}H_{22}N_2$ Calc'd: C, 80.27; H, 8.72; N, 11.01. Found: C, 80.18; H, 8.87; N, 10.76.

EXAMPLE 6

2,3,4,5,9,10,11,12-Octahydro-1H-[1,4]diazocino[7,8,1-jk]carbazole

To a solution of 3-methyl-2,3,4,5,9,10,11,12-octahydro-1H-[1,4]diazocino[7,8,1-jk]carbazole (0.20 g, 0.79 mmole) in dichloroethane (15 mL) was added 1-chloroethyl chloroformate (0.80 mL, 7.2 mmole) and the solution refluxed for 24 hours under nitrogen. The reaction mixture was cooled to room temperature and the solvent removed in vacuo and replaced with methanol (100 mL) and refluxed for another 3 hours under nitrogen. The solvent was removed in vacuo and the residue purified by flash column chromatography (silica gel, 1.5% methanol in dichloromethane) to provide 0.10 g of the title compound as a light yellow oil. The oil was further treated with one equivalent of fumaric acid in ethanol, the resulting solid collected by filtration and washed with ether to give 0.12 g of a fumarate salt, mp 174–176° C. MS (ESI) m/z 241 ([M+H]+).

Elemental Analysis for: $C_{16}H_{20}N_2 \cdot C_4H_4O_4 \cdot 0.20\ C_4H_{10}O$ Calc'd: C, 67.29; H, 7.06; N, 7.55. Found: C, 67.50; H, 6.99; N, 7.42.

EXAMPLE 7

3-Methyl-2,3,4,5,8b,9,10,11,12,12a-decahydro-1H-[1,4]diazocino[7,8,1-jk]carbazole To a solution of 3-methyl-2,3,4,5,9,10,11,12-octahydro-1H-[1,4]diazocino[7,8,1-jk]carbazole (0.46 g, 1.8 mmole) in acetic acid (50 mL) was added sodium cyanoborohydride (0.30 g, 4.5 mmol) and the reaction mixture was stirred at room temperature for 1 hour. The solvent was removed in vacuo and the residue was diluted with ethyl acetate (300 mL) and washed with saturated aqueous sodium bicarbonate (150 mL) and saturated aqueous sodium chloride (150 mL), dried (sodium sulfate) and concentrated in vacuo. Purification by flash column chromatography (silica gel, ethyl acetate:hexanes 3:2) provided 0.30 g of the title compound as a light oil. 100 mg of this compound was treated with one equivalent of fumaric acid in ethanol to form a fumarate salt, mp 150–153° C. MS (ESI) m/z 257 ([M+H]+).

Elemental Analysis for: $C_{17}H_{24}N_2 \cdot C_4H_4O_4$ Calc'd: C, 67.72; H, 7.58; N, 7.52. Found: C, 67.67; H, 7.66; N, 7.27.

EXAMPLE 8

2,3,4,5,8b,9,10,11,12,12a-Decahydro-1H-[1,4]diazocino[7,8,1-jk]carbazole

To a solution 2,3,4,5,9,10,11,12-octahydro-1H-[1,4]diazocino[7,8,1-jk]carbazole (0.20 g, 0.80 mmole) in acetic acid (50 mL) was added sodium cyanoborohydride (0.30 g, 4.5 mmol) and the reaction mixture was stirred at room temperature for 1 hour. The solvent was removed in vacuo and the residue was diluted with ethyl acetate (300 mL) and washed with saturated aqueous sodium bicarbonate (150 mL) and saturated aqueous sodium chloride (150 mL), dried (sodium sulfate) and concentrated in vacuo. Purification by flash column chromatography (silica gel, ethyl acetate:hexanes 3:2) provided 0.12 g of the title compound as an oil. This compound was treated with one equivalent of fumaric acid in ethanol to form a fumarate salt, mp 169–171° C. MS (ESI) m/z 243 ([M+H]+).

Elemental Analysis for: $C_{16}H_{22}N_2.C_4H_4O_4$ Calc'd: C, 67.02; H, 7.31; N, 7.82. Found: C, 66.87; H, 7.38; N, 7.63.

EXAMPLE 9

3-Methyl-2,3,4,5,10,11,12,13-octahydro-1H,9H-cyclohepta[b][1,4]diazocino[7,8,1-hi]indole To a solution of 4-methyl-3,4,5,6-tetrahydro-2H-benzo[e][1,4]diazocin-1-ylamine (1.80 g, 9.4 mmol) in 1-propanol (100 mL) was added cycloheptanone (5.28 g, 47.0 mmole), followed by p-toluenesulfonic acid monohydrate (3.2 g, 16.8 mmole), and the resulting reaction mixture was refluxed for 40 hours. The reaction mixture was cooled to room temperature and solvent removed in vacuo to produce a brown residue. The residue was diluted with ethyl acetate (300 mL) and washed with saturated aqueous sodium bicarbonate (150 mL), saturated aqueous sodium chloride (150 mL), dried (sodium sulfate) and concentrated in vacuo. Purification by flash column chromatography (silica gel, ethyl acetate:hexanes 1:1) provided 1.20 g of the title compound as a light yellow solid. 80 mg of this was treated with one equivalent of fumaric acid in ethanol to form a fumarate salt, mp 190–192° C. MS (ESI) m/z 269 ([M+H]+).

Elemental Analysis for: $C_{18}H_{24}N_2.C_4H_4O_4.0.20\ H_2O$ Calc'd: C, 68.09; H, 7.38; N, 7.22. Found: C, 68.09; H, 7.17; N, 7.01.

EXAMPLE 10

2,3,4,5,10,11,12,13-Octahydro-1H,9H-cyclohepta[b]1,4]diazocino[7,8,1-hi]indole To a solution of 3-methyl-2,3,4,5,10,11,12,13-octahydro-1H,9H-cyclohepta[b][1,4]diazocino[7,8,1-hi]indole (0.15 g, 0.56 mmole) in dichloroethane (15 mL) was added 1-chloroethyl chloroformate (0.80 mL, 7.2 mmole) and the solution refluxed for 24 hours under nitrogen. The reaction mixture was cooled to room temperature and the solvent removed in vacuo and replaced with methanol (100 mL) and refluxed for another 3 hours under nitrogen. The solvent was removed in vacuo and the residue purified by flash column chromatography (silica gel, 1.5% methanol in dichloromethane) to provide 60 mg of the title compound as a light yellow oil. This was further treated with one equivalent of fumaric acid in ethanol to form a fumarate salt, mp 216–218° C. MS (ESI) m/z 255 ([M+H]+).

Elemental Analysis for: $C_{17}H_{22}N_2.C_4H_4O_4$ Calc'd: C, 68.09; H, 7.07; N, 7.56. Found: C, 68.03; H, 6.93; N, 7.41.

EXAMPLE 11

3-Methyl-2,3,4,5,11,12-hexahydro-1H,9H-[1,4]diazocino[7,8,1-hi]thiopyrano[4,3-b]indole To a solution of 4-methyl-3,4,5,6-tetrahydro-2H-benzo[e][1,4]diazocin-1-ylamine (1.50 g, 8.1 mmole) in 1-propanol (100 mL) was added tetrahydro-thiopyran-4-one (5.0 g, 43 mmole), followed by p-toluenesulfonic acid monohydrate (3.2 g, 16.8 mmole), and the resulting reaction mixture was refluxed for 40 hours. The reaction mixture was cooled to room temperature and solvent removed in vacuo to produce a brown residue. The residue was diluted with ethyl acetate (300 mL) and washed with saturated aqueous sodium bicarbonate (150 mL), saturated aqueous sodium chloride (150 mL), dried (sodium sulfate) and concentrated in vacuo. Purification by flash column chromatography (silica gel, ethyl acetate:hexanes 1:1) provided 0.52 g of the title compound as an off-white solid, mp 123–125° C., with a trace of ethyl acetate. MS (ESI) m/z 273 ([M+H]+).

Elemental Analysis for: $C_{16}H_{20}N_2S.0.20\ C_4H_8O_2$ Calc'd: C, 69.57; H, 7.51; N, 9.66. Found: C, 69.40; H, 7.27; N, 9.64.

Intermediate 2

2-(2-Chloro-6-nitro-phenyl)-ethanol

To a solution of 1-chloro-2-methyl-3-nitrobenzene (171.6 g, 1.0 mole) in DMSO (150 mL) was added paraformaldehyde (30.0 g, 1.0 mole), followed by potassium hydroxide (1.5 g, 0.027 mole in ethanol (10 mL). The resulting reaction mixture was stirred at room temperature for six days and water (2 L) was added and the mixture neutralized with hydrochloric acid (2 N). The mixture was extracted with ethyl ether (2×1 L) and the combined organic layers were washed with water (1 L), saturated sodium chloride (1 L), dried (sodium sulfate) and concentrated to a yellow solid. Purification by flash column chromatography (silica gel, methylene chloride:hexanes 1:2) provided 110.0 g of a mixture of starting material and product and then 66.0 g of the title compound as a yellow solid. $^1$H NMR (DMSO-d$_6$): 7.80 δ (m, 2H); 7.45 δ (t, 1H); 4.90 δ (broad, 1H); 3.55 δ (t, 2H); 3.05 δ (t, 2H).

Intermediate 3

2-(2-Bromo-ethyl)-1-chloro-3-nitro-benzene

To a solution of 2-(2-chloro-6-nitrophenyl)ethanol (33.0 g, 0.16 mole) in methylene chloride (500 mL) was added triphenylphosphine (43.0 g, 0.16 mole) and the mixture was cooled to 0° C. Carbon tetrabromide (54.4 g, 0.16 mole) in methylene chloride (100 mL) was added dropwise through an addition funnel. The reaction mixture was stirred at room temperature overnight. The solvent was removed in vacuo and the residue purified by flash column chromatography (silica gel, ethyl acetate:hexanes 1:9) to provide 39.0 g of the title compound as a yellow solid. $^1$H NMR (CDCl$_3$): 7.70 δ (d, 1H); 7.60 δ (d, 1H); 7.35 δ (t, 1H); 3.60 δ (t, 2H); 3.45 δ (t, 2H).

Intermediate 4

[2-(2-Chloro-6-nitro-phenyl)-ethyl]-methyl-amine

To a solution of methylamine in THF (2 M, 200 mL) was added 2-(2-bromoethyl)-1-chloro-3-nitro-benzene (14.0 g, 0.053 mole) in a pressure bottle, the reaction mixture was stirred at 60° C. overnight and the solvent was removed. The solid residue was treated with sodium hydroxide (1 N, 100 mL) and the aqueous extracted with methylene chloride (2×100 mL). The combined organic layers were washed with water (100 mL), saturated sodium chloride (100 mL), dried (sodium sulfate) and concentrated to provide 11.0 g of the title compound as a light brown oil. $^1$H NMR (DMSO-d$_6$): 7.70 δ (d, 1H); 7.60 δ (d, 1H); 7.35 δ (t, 1H); 3.15 δ (t, 2H); 2.90 δ (t, 2H); 2.60 δ (s, 3H); 1.60 δ (broad, 1H).

Intermediate 5

{[2-(2-Chloro-6-nitro-phenyl)-ethyl]-methyl-amino}-acetic acid ethyl ester

A solution of [2-(2-chloro-6-nitro-phenyl)-ethyl]-methylamine (11.0 g, 0.051 mole) and ethyl bromoacetate (8.56 g, 0.051 mole) in acetonitrile (200 mL) containing potassium carbonate (3.54 g, 0.026 mole) was stirred at room temperature overnight. The mixture was evaporated in vacuo, water was added to the residue, this mixture was made basic with sodium carbonate and then extracted with dichloromethane (2×300 mL), the combined organic layers were washed with saturated sodium chloride (300 mL), dried and concentrated. Purification by flash column chromatography (silica gel, methylene chloride:hexanes 1:1) provided 9.0 g of the title compound as a light brown oil. $^1$H NMR (CDCl$_3$): 7.70 δ (d, 1H); 7.60 δ (d, 1H); 7.35 δ (t, 1H); 4.20 δ (m, 2H); 3.35 δ (s, 2H); 3.15 δ (t, 2H); 2.90 δ (t, 2H); 2.50 δ (s, 3H); 1.30 δ (t, 3H).

Intermediate 6

{[2-(2-chloro-6-nitro-phenyl)-ethyl]-methyl-amino}-acetic acid

{[2-(2-chloro-6-nitro-phenyl)-ethyl]-methyl-amino}-acetic acid ethyl ester (11.0 g, 0.0365 mole) dissolved in concentrated hydrobromic acid (48 wt. % in water, 200 mL) was allowed to stir at 70° C. overnight and then reduced to a small volume in vacuo. The residue oil was taken up in acetonitrile and the solution was evaporated in vacuo. This procedure was repeated until the water was removed and a crystalline residue remained. This material was used in the next step without further purification.

Intermediate 7

7-Chloro-4-methyl-3,4,5,6-tetrahydro-1H-benzo[e][1,4]diazocin-2-one

{[2-(2-chloro-6-nitro-phenyl)-ethyl]-methyl-amino}-acetic acid (12 g, approximately 0.049 molE, not quite pure) in methanol (250 mL) containing platinum on sulfided carbon (5 wt. %, 1.2 g) was hydrogenated at room temperature and a hydrogen pressure of 50 psi overnight. The catalyst was removed by filtration through Celite and the filtrate was evaporated to dryness in vacuo. The residue was dissolved in pyridine (1.5 L) and the solution was cooled to 0° C., and 1,3-dicyclohexylcarbodiimide (20.0 g, 0.097 mole) was added. The reaction mixture was allowed to warm up to room temperature and stirred at room temperature for 48 hours. The solvent was removed and the residue was slurried with 10% hydrochloric acid and filtered. The filtrate was extracted with ether, the aqueous phase was made basic with sodium carbonate and then extracted with dichloromethane. The extract was dried over sodium sulfate and evaporated in vacuo. Purification by flash column chromatography (silica gel, methylene chloride) provided 4.0 g of the title compound as a white solid. $^1$H NMR (CDCl$_3$): 7.50 δ (broad, 1H); 7.30 δ (d, 1H); 7.20 δ (s, 1H); 7.00 δ (d, 1H); 3.18 δ (s, 2H); 2.80 δ (broad s, 4H); 2.40 δ (s, 3H). MS(ES) m/z 225 ([M+H]+).

Intermediate 8

7-Chloro-4-methyl-1,2,3,4,5,6-hexahydro-benzo[e][1,4]diazocine

A solution of the lactam 7-chloro-4-methyl-3,4,5,6-tetrahydro-1H-benzo[e][1,4]diazocin-2-one (4.0 g, 0.021 mole) in THF (100 mL) was added dropwise to a stirred suspension of lithium aluminum hydride (2.5 g, 0.063 mol) in THF (100 mL). The resulting mixture was stirred at reflux for 3 hours and the excess hydride was destroyed at 0° C. by the cautious addition of water. The mixture was diluted with THF (200 mL) and filtered. Evaporation of the filtrate in vacuo provided the title compound as a light yellow oil.

Intermediate 9

7-Chloro-4-methyl-3,4,5,6-tetrahydro-2H-benzo[e][1,4]diazocin-1-ylamine

To a solution of 7-chloro-4-methyl-1,2,3,4,5,6-hexahydro-benzo[e][1,4]diazocine (4.0 g, 0.021 mole approximately) in hydrochloric acid (2 N, 100 mL) cooled to 0° C. was added sodium nitrite (2.5 g, 0.036 mole) in water (20 mL). The mixture was stirred for 1 hour and treated with sodium bicarbonate and extracted with ethyl acetate (3×100 mL). The combined organic layers were washed with saturated sodium chloride (200 mL), dried and concentrated to a light brown oil. The oil was redissolved in THF (50 mL) and added to a suspension of lithium aluminum hydride (2.5 g, 0.063 mole) in THF (100 mL) and the mixture refluxed for 3 hours. The excess hydride was destroyed at 0° C. by the cautious addition of water. The mixture was diluted with THF (200 mL) and filtered. Evaporation of the filtrate in vacuo provided 3.5 g of the title compound as a light yellow oil. This oil was used for indole formation without further purification. MS (ES) m/z 226.5 ([M+H]$^+$).

EXAMPLE 12

6-Chloro-3-methyl-2,3,4,5,10,11-hexahydro-1H,9H-cyclopenta[b][1,4]diazocino[7,8,1-hi]indole To a solution of 7-chloro-4-methyl-3,4,5,6-tetrahydro-2H-benzo[e][1,4]diazocin-1-ylamine (1.20 g, 5.32 mmole) in 1-propanol (100 mL) was added cyclopentanone (6.66 g, 79.14 mmole) followed by p-toluenesulfonic acid monohydrate (3.2 g, 16.8 mmole) and the resulting reaction mixture was refluxed for 24 hours. The reaction mixture was cooled to room temperature and solvent removed in vacuo to produce a brown residue. The residue was diluted with ethyl acetate (300 mL) and washed with saturated sodium bicarbonate (150 mL), saturated sodium chloride (150 mL), dried (sodium sulfate) and concentrated. Purification by flash column chromatography (silica gel, ethyl acetate:hexanes 1:1) provided 0.20 g of the title compound as a white solid, mp 138–140° C.

MS (ESI) m/z 275 ([M+H]+). Elemental Analysis for: $C_{16}H_{19}ClN_2$ Calc'd: C, 69.93; H, 6.97; N, 10.19. Found: C, 70.01; H, 7.12; N, 10.15.

EXAMPLE 13

6-Chloro-3-methyl-2,3,4,5,9,10,11,12-octahydro-1H-[1,4]diazocino[7,8,1-jk]carbazole To a solution of 7-chloro-4-methyl-3,4,5,6-tetrahydro-2H-benzo[e][1,4]diazocin-1-ylamine (1.20 g, 5.32 mmole) in 1-propanol (100 mL) was added cyclohexanone (4.73 g, 48.2 mmole) followed by p-toluenesulfonic acid monohydrate (3.2 g, 16.8 mmole) and the resulting reaction mixture was refluxed for 24 hours. The reaction mixture was cooled to room temperature and solvent removed in vacuo to produce a brown residue. The residue was diluted with ethyl acetate (300 mL) and washed with saturated sodium bicarbonate (150 mL), saturated sodium chloride (150 mL), dried (sodium sulfate) and concentrated. Purification by flash column chromatography (silica gel, ethyl acetate:hexanes 1:1) provided 0.52 g of the title compound as a white solid, mp 128–130° C.

MS (ESI) m/z 289 ([M+H]+). Elemental Analysis for: $C_{17}H_{21}ClN_2 \cdot 0.08\ C_6H_{14}$ Calc'd: C, 71.00; H, 7.54; N, 9.47. Found: C, 70.92; H, 7.74; N, 9.50.

EXAMPLE 14

6-Chloro-3-methyl-2,3,4,5,10,11,12,13-octahydro-1H,9H-cyclohepta[b][1,4]diazocino[7,8,1-hi]indole To a solution of 7-chloro-4-methyl-3,4,5,6-tetrahydro-2H-benzo[e][1,4]diazocin-1-ylamine (1.20 g, 5.32 mmole) in 1-propanol (100 mL) was added cycloheptanone (6.65 g, 59.3 mmole) followed by p-toluenesulfonic acid monohydrate (3.2 g, 16.8 mmol) and the resulting reaction mixture was refluxed for 24 hours. The reaction mixture was cooled to room temperature and solvent removed in vacuo to produce a brown residue. The residue was diluted with ethyl acetate (300 mL) and washed with saturated sodium bicarbonate (150 mL), saturated sodium chloride (150 mL), dried (sodium sulfate) and concentrated. Purification by flash column chromatography (silica gel, ethyl acetate:hexanes 1:1) provided 0.55 g of the title compound as a white solid, mp 132–134° C. MS (ESI) m/z 303 ([M+H]+).

Elemental Analysis for: $C_{18}H_{23}ClN_2$ Calc'd: C, 71.39; H, 7.66; N, 9.25. Found: C, 71.24; H, 7.66; N, 9.13.

EXAMPLE 15

6-Chloro-3-Methyl-2,3,4,5,9,10,11,11a-octahydro-1H,8bH-cyclopenta[b][1,4]diazocino[7,8,1-hi]indole To a solution of 6-chloro-3-methyl-2,3,4,5,10,11-hexahydro-1H,9H-cyclopenta[b][1,4]diazocino[7,8,1-hi]indole (0.20 g, 0.73 mmole) in acetic acid (50 mL) was added excess sodium cyanoborohydride (0.23 g, 3.65 mmole) and the reaction mixture was stirred at room temperature for 5 hours. The solvent was removed in vacuo and the residue was diluted with ethyl acetate (200 mL) and washed with saturated sodium bicarbonate (150 mL), saturated sodium chloride (150 mL), dried (sodium sulfate) and concentrated. Purification by flash column chromatography (silica gel, ethyl acetate:hexanes 3:2) provided 66 mg of the title compound. This was further treated with one equivalent of fumaric acid in ethanol to form a fumarate salt, mp 196–9° C. MS (ESI) m/z 277 ([M+H]+).

Elemental Analysis for: $C_{16}H_{21}ClN_2 \cdot C_4H_4O_4 \cdot 0.15\ H_2O$ Calc'd: C, 60.73; H, 6.45; N, 7.08. Found: C, 60.73; H, 6.35; N, 6.84.

EXAMPLE 16

6-Chloro-3-methyl-2,3,4,5,9,10,11,12,13,13a-decahydro-1H,8bH-cyclohepta[b][1,4]diazocino[7,8,1-hi]indole To a solution of 6-chloro-3-methyl-2,3,4,5,10,11,12,13-octahydro-1H,9H-cyclohepta[b][1,4]diazocino[7,8,1-hi]indole (0.20 g, 0.66 mmole) in acetic acid (50 mL) was added excess sodium cyanoborohydride (0.21 g, 3.3 mmole) and the reaction mixture was stirred at room temperature for 5 hours. The solvent was removed in vacuo and the residue was diluted with ethyl acetate (200 mL) and washed with saturated sodium bicarbonate (150 mL), saturated sodium chloride (150 mL), dried (sodium sulfate) and concentrated. Purification by flash column chromatography (silica gel, ethyl acetate:hexanes 3:2) provided 0.17 g of the title compound. This was further treated with one equivalent of fumaric acid in ethanol to form a fumarate salt, mp 190–193° C. MS (ESI) m/z 305 ([M+H]+).

Elemental Analysis for: $C_{18}H_{25}ClN_2 \cdot C_4H_4O_4$ Calc'd: C, 62.77; H, 6.94; N, 6.65. Found: C, 62.42; H, 7.02; N, 6.52.

EXAMPLE 17

6-Chloro-2,3,4,5,10,11-hexahydro-1H,9H-cyclopenta[b][1,4]diazocino[7,8,1-hi]indole To a solution of 6-chloro-3-methyl-2,3,4,5,10,11-hexahydro-1H,9H-cyclopenta[b][1,4]diazocino[7,8,1-hi]indole (0.33 g, 1.20 mmole) in dichloroethane (80 mL) was added 1-chloroethyl chloroformate (1.2 mL, 10.8 mmole) and the mixture refluxed for 24 hours. The reaction mixture was cooled to room temperature and the solvent removed in vacuo and replaced with methanol (25 mL) and refluxed for another 3 hours. The reaction mixture was then cooled to room temperature and the solvent removed in vacuo. The dark residue was dissolved in methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% methanol in dichloromethane) provided 0.25 g of the title compound. 46 mg of this was further treated with one equivalent of fumaric acid in ethanol to form a fumarate salt, mp 188–190° C. MS (ESI) m/z 261 ([M+H]+).

Elemental Analysis for: $C_{15}H_{17}ClN_2 \cdot C_4H_4O_4 \cdot 0.08\ C_2H_6O$ Calc'd: C, 60.48; H, 5.69; N, 7.36. Found: C, 60.90; H, 5.75; N, 6.95.

EXAMPLE 18

6-Chloro-2,3,4,5,9,10,11,12-octahydro-1H-[1,4]diazocino[7,8,1-jk]carbazole

To a solution of 6-chloro-3-methyl-2,3,4,5,9,10,11,12-octahydro-1H-[1,4]diazocino[7,8,1-jk]carbazole (0.36 g, 1.25 mmole) in dichloroethane (80 mL) was added 1-chloroethyl chloroformate (1.2 mL, 10.8 mmole) and the mixture refluxed for 24 hours. The reaction mixture was cooled to room temperature and the solvent removed in vacuo and replaced with methanol (25 mL) and refluxed for another 3 hours. The reaction mixture was then cooled to room temperature and the solvent removed in vacuo. The dark residue was dissolved in methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% methanol in dichloromethane) provided 0.30 g of the title compound. 80 mg of this was further treated with one equivalent of fumaric acid in ethanol to form a fumarate salt, mp 208–210° C. MS (ESI) m/z 275 ([M+H]+).

Elemental Analysis for: $C_{16}H_{19}ClN_2 \cdot C_4H_4O_4 \cdot 0.80\ C_2H_6O \cdot 0.30\ H_2O$ Calc'd: C, 59.90; H, 6.61; N, 6.47. Found: C, 60.04; H, 6.36; N, 6.12.

EXAMPLE 19

6-Chloro-2,3,4,5,10,11,12,13-octahydro-1H,9H-cyclohepta[b][1,4]diazocino[7,8,1-hi]indole To a solution of 6-chloro-3-methyl-2,3,4,5,10,11,12,13-octahydro-1H,9H-cyclohepta[b][1,4]diazocino[7,8,1-hi]indole (0.30 g, 0.99 mmole) in dichloroethane (80 mL) was added 1-chloroethyl chloroformate (1.2 mL, 10.8 mmole) and the mixture refluxed for 24 hours. The reaction mixture was cooled to room temperature and the solvent removed in vacuo and replaced with methanol (25 mL) and refluxed for another 3 hours. The reaction mixture was then cooled to room temperature and the solvent removed in vacuo. The dark residue was dissolved in methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% methanol in dichloromethane) provided 0.28 g of the title compound. 88 mg of this was further treated with one equivalent of fumaric acid in ethanol to form a fumarate salt, mp 208–210° C. MS (ESI) m/z 289 ([M+H]+).

Elemental Analysis for: $C_{17}H_{21}ClN_2.C_4H_4O_4$ Calc'd: C, 62.30; H, 6.22; N, 6.92. Found: C, 62.22; H, 6.37; N, 6.77.

EXAMPLE 20

6-Chloro-2,3,4,5,9,10,11,11a-octahydro-1H,8bH-cyclopenta[b][1,4]diazocino[7,8,1-hi]indole To a solution of 6-chloro-2,3,4,5,10,11-hexahydro-1H,9H-cyclopenta[b][1,4]diazocino[7,8,1-hi]indole (0.20 g, 0.77 mmole) in acetic acid (50 mL) was added excess sodium cyanoborohydride (0.48 g, 3.85 mmole) and the reaction mixture was stirred at room temperature overnight. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5–5% methanol in methylene chloride) collected two components. The second component weighed 36 mg and was characterized as the title compound. This compound was treated with one equivalent of fumaric acid in ethanol to form a fumarate salt, mp 188–189° C. MS (ESI) m/z 263 ([M+H]+).

Elemental Analysis for: $C_{15}H_{19}ClN_2.C_4H_4O_4$ Calc'd: C, 60.24; H, 6.12; N, 7.39. Found: C, 60.40; H, 6.29; N, 7.15.

EXAMPLE 21

6-Chloro-3-ethyl-2,3,4,5,9,10,11,11a-octahydro-1H, 8bH-cyclopenta[b][1,4]diazocino[7,8,1-hi]indole The first component from the chromatography described in Example 20 weighed 85 mg and was characterized as the title compound. This compound was treated with one equivalent of fumaric acid in ethanol to form a fumarate salt, mp 199–201° C. MS (ESI) m/z 291 ([M+H]+).

Elemental Analysis for: $C_{17}H_{23}ClN_2.C_4H_4O_4$ Calc'd: C, 61.99; H, 6.69; N, 6.88. Found: C, 62.02; H, 6.77; N, 6.72.

EXAMPLE 22

6-Chloro-2,3,4,5,9,10,11,12,13,13a-decahydro-1H, 8bH-cyclohepta[b][1,4]diazocino[7,8,1-hi]indole To a solution of 6-chloro-2,3,4,5,10,11,12,13-octahydro-1H,9H-cyclohepta[b][1,4]diazocino[7,8,1-hi]indole (0.20 g, 0.69 mmole) in acetic acid (50 mL) was added excess sodium cyanoborohydride (0.21 g, 3.45 mmole) and the reaction mixture was stirred at room temperature for 5 hours. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 5% methanol in methylene chloride) provided 67 mg of the title compound. This compound was treated with one equivalent of fumaric acid in ethanol to form a fumarate salt, mp 168–170° C. MS (ESI) m/z 291 ([M+H]+).

Elemental Analysis for: $C_{17}H_{23}ClN_2.C_4H_4O_4$ Calc'd: C, 61.99; H, 6.69; N, 6.88. Found: C, 61.83; H, 6.75; N, 6.77.

EXAMPLE 23

6-Chloro-3-ethyl-2,3,4,5,8b,9,10,11,12,12a-decahydro-1H-[1,4]diazocino[7,8,1-jk]carbazole To a solution of 6-chloro-2,3,4,5,9,10,11,12-octahydro-1H-[1,4]diazocino[7,8,1-jk]carbazole (0.20 g, 0.73 mmole) in acetic acid (50 mL) was added excess sodium cyanoborohydride (0.23 g, 3.65 mmole) and the reaction mixture was stirred at room temperature overnight. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 5% methanol in methylene chloride) provided 0.10 g of the title compound. This compound was treated with one equivalent of fumaric acid in ethanol to form a fumarate salt, mp 184–187° C. MS (ESI) m/z 305 ([M+H]+).

Elemental Analysis for: $C_{18}H_{25}ClN_2.C_4H_4O_4$ Calc'd: C, 62.77; H, 6.94; N, 6.65. Found: C, 62.65; H, 7.07; N, 6.53.

Intermediate 10

2-(4-Fluoro-2-nitro-phenyl)-ethanol

To a solution of 4-fluoro-1-methyl-2-nitrobenzene (73.2 g, 0.47 mole) in DMSO (75 mL) was added paraformaldehyde (14.1 g, 0.47 mole), followed by potassium hydroxide (0.75 g) in ethanol (5 mL). The resulting reaction mixture was stirred at room temperature for six days and water (2 L) was added and the mixture neutralized with hydrochloric acid (2 N). The mixture was extracted with ethyl acetate (1 L) and the combined organic layers were washed with water (1 L), saturated sodium chloride (500 mL), dried (sodium sulfate) and concentrated to a yellow solid. Purification by flash column chromatography (silica gel, 1:1 methylene chloride:hexanes to methylene chloride) provided 20.7 g of the title compound as a light yellow oil. $^1$H NMR (CDCl$_3$): 7.63 δ (dd, 1H); 7.40 δ (dd, 1H); 7.28 δ (dd, 1H); 3.90 δ (t, 3H); 3.10 δ (t, 2H); 1.55 δ (broad, 1H).

Intermediate 11

1-(2-Bromo-ethyl)-4-fluoro-2-nitro-benzene

To a solution of 2-(4-fluoro-2-nitro-phenyl)-ethanol (20.7, 0.11 mole) in methylene chloride (500 mL) was added triphenylphosphine (30.0 g, 0.11 mole) and the mixture was cooled to 0° C. Carbon tetrabromide (40.0 g, 0.12 mole) in methylene chloride (100 mL) was added dropwise through an addition funnel. The reaction mixture was stirred at room temperature overnight. The solvent was removed in vacuo and the residue purified by flash column chromatography (silica gel, ethyl acetate:hexanes 3:7) to provide 24.0 g of the title compound as a yellow solid. $^1$H NMR (CDCl$_3$): 7.70 δ (d, 1H); 7.40 δ (dd, 1H); 7.30 δ (d of t, 1H); 3.65 δ (t, 2H); 3.40 δ (t, 2H).

Intermediate 12

[2-(4-Fluoro-2-nitro-phenyl)-ethyl]-methyl-amine

To a solution of methylamine in THF (2 M, 200 mL) was added 1-(2-bromo-ethyl)-4-fluoro-2-nitro-benzene (13.2 g, 0.053 mole) in a pressure bottle, the reaction mixture was stirred at 60° C. overnight and the solvent was removed. The solid residue was treated with sodium hydroxide (1 N, 100 mL) and the aqueous extracted with methylene chloride (2×100 mL). The combined organic layers were washed with water (100 mL), saturated sodium chloride (100 mL), dried (sodium sulfate) and concentrated to provide 10.4 g of the title compound as a dark brown oil. $^1$H NMR (DMSO-$d_6$): 7.60 δ (dd, 1H); 7.35 δ (dd, 1H); 7.20 δ (d of t, 1H); 3.05 δ (t, 2H); 2.85 δ (t, 2H); 2.40 δ (s, 3H); 1.60 δ (broad, 1H).

Intermediate 13

{[2-(4-Fluoro-2-nitro-phenyl)-ethyl]-methyl-amino}-acetic acid ethyl ester

A solution of [2-(4-fluoro-2-nitro-phenyl)-ethyl]-methyl-amine (10.4 g, 0.053 mole) and ethyl bromoacetate (8.8 g, 0.053 mole) in acetonitrile (200 mL) containing potassium carbonate (3.64 g, 0.026 mole) was stirred at room temperature overnight. The mixture was evaporated in vacuo, water was added to the residue and then extracted with dichloromethane (2×200 mL). The combined organic layers were washed with saturated sodium chloride (300 mL), dried and concentrated. Purification by flash column chromatography (silica gel, methylene chloride:hexanes 1:1 to methylene chloride) provided 10.0 g of the title compound as a light brown oil. $^1$H NMR (CDCl$_3$): 7.65 δ (dd, 1H); 7.40 δ (dd, 1H); 7.25 δ (dd, 1H); 4.20 δ (m, 2H); 3.30 δ (s, 2H); 3.05 δ (t, 2H); 2.80 δ (t, 2H); 2.45 δ (s, 3H); 1.25 δ (t, 3H).

Intermediate 14

{[2-(4-Fluoro-2-nitro-phenyl)-ethyl]-methyl-amino}-acetic acid

{[2-(4-Fluoro-2-nitro-phenyl)-ethyl]-methylamino}-acetic acid ethyl ester (10.0 g, 0.035 mole) dissolved in concentrated hydrobromic acid (48 wt. % in water, 200 mL) was allowed to stir at 70° C. overnight and then reduced to a small volume in vacuo. The residue oil was taken up in acetonitrile and the solution was evaporated in vacuo. This procedure was repeated until the water was removed and a crystalline residue remained. This material was used in the next step without further purification. $^1$H NMR (DMSO): 8.00 δ (dd, 1H); 7.65 δ (m, 2H); 4.20 δ (s, 2H); 3.40 δ (large water peak obscure some aliphatic resonances); 3.20 δ (t, 2H); 2.90 δ (s, 3H).

Intermediate 15

9-Fluoro-4-methyl-3,4,5,6-tetrahydro-1H-benzo[e][1,4]diazocin-2-one

{[2-(4-Fluoro-2-nitro-phenyl)-ethyl]-methyl-amino}-acetic acid (10.0 g, approximately 0.044 mole, not quite pure) in methanol (250 mL) containing platinum on sulfided carbon (5 wt. %, 1.2 g) was hydrogenated at room temperature and a hydrogen pressure of 50 psi overnight. The catalyst was removed by filtration through Celite and the filtrate was evaporated to dryness in vacuo. The residue was dissolved in pyridine (1.5 L) and the solution was cooled to 0° C., and 1,3-dicyclohexylcarbodiimide (20.0 g, 0.097 mole) was added. The reaction mixture was allowed to warm up to room temperature and stirred at room temperature for 48 hours. The solvent was removed and the residue was slurried with 10% hydrochloric acid and filtered. The filtrate was extracted with ether, the aqueous phase was made basic with sodium carbonate and then extracted with dichloromethane. The extract was dried over sodium sulfate and evaporated in vacuo. Purification by flash column chromatography (silica gel, methylene chloride) provided 2.0 g of the title compound as a white solid. $^1$H NMR (CDCl$_3$): 7.85 δ (broad s, 1H); 7.15 δ (dd, 1H); 6.95 δ (d of t, 1H); 6.80 δ (dd, 1H); 3.18 δ (s, 2H); 2.78 δ (broad s, 4H); 2.40 δ (s, 3H).

Intermediate 16

9-Fluoro-4-methyl-1,2,3,4,5,6-hexahydro-benzo[e][1,4]diazocine

A solution of the lactam 9-fluoro-4-methyl-3,4,5,6-tetrahydro-1H-benzo[e][1,4]diazocin-2-one (2.0 g, 0.0096 mole) in THF (100 mL) was added dropwise to a stirred suspension of lithium aluminum hydride (1.2 g) in THF (100 mL). The resulting mixture was stirred at reflux for 3 hours and the excess hydride was destroyed at 0° C. by the cautious addition of ethyl acetate. The mixture was washed with aqueous potassium sodium tartrate (10% v/w, 150 mL) and saturated aqueous sodium chloride (150 mL), dried (sodium sulfate) and concentrated. Evaporation of in vacuo provided 1.9 g of the title compound as a light yellow oil.

Intermediate 17

9-Fluoro-4-methyl-3,4,5,6-tetrahydro-2H-benzo[e][1,4]diazocin-1-ylamine

To a solution of 9-Fluoro-4-methyl-1,2,3,4,5,6-hexahydro-benzo[e][1,4]diazocine (1.9 g, 0.0096 mole approximately) in hydrochloric acid (2 N, 100 mL) cooled to 0° C. was added sodium nitrite (2.5 g, 0.036 mole) in water (20 mL). The mixture was stirred for 1 hour and treated with sodium bicarbonate and extracted with ethyl acetate (3×100 mL). The combined organic layers were washed with saturated sodium chloride (200 mL), dried and concentrated to a light brown oil. The oil was redissolved in THF (50 mL) and added to a suspension of lithium aluminum hydride (2.5 g, 0.063 mole) in THF (100 mL) and the mixture refluxed for 3 hours. The excess hydride was destroyed at 0° C. by the cautious addition of ethyl acetate. The mixture was washed with aqueous potassium sodium tartrate (10% v/w, 150 mL) and saturated aqueous sodium chloride (150 mL), dried (sodium sulfate) and concentrated. Evaporation in vacuo provided 1.9 g of the title compound as a light yellow oil. This oil was used for indole formation without further purification. MS (ES) m/z 210.1 ([M+H]$^+$).

EXAMPLE 24

8-Fluoro-3-methyl-2,3,4,5,10,11-hexahydro-1H,9H-cyclopenta[b][1,4]diazocino[7,8,1-hi]indole To a solution of 9-fluoro-4-methyl-3,4,5,6-tetrahydro-2H-benzo[e][1,4]diazocin-1-ylamine (4.0 g, 19.1 mmole) in 1-propanol (300 mL) was added cyclopentanone (14.3 ml, 169.6 mmole), followed by p-toluenesulfonic acid monohydrate (10.3 g, 53.3 mmole), and the resulting reaction mixture was refluxed for 30 hours. The reaction mixture was cooled to room temperature and solvent removed in vacuo to produce a brown residue. The residue was diluted with ethyl acetate (500 mL) and washed with saturated aqueous sodium bicarbonate (350 mL), saturated aqueous sodium chloride (350 mL), dried (sodium sulfate) and concentrated in vacuo. Purification by flash column chromatography (silica gel, ethyl acetate:hexanes 1:1) provided 1.0 g of the title compound. 70.5 mg of the free amine was treated with one equivalent of fumaric acid in ethanol to form a fumarate salt, mp 168–170° C. MS (ES) m/z 259.12 ([M+H]$^+$).

Elemental Analysis for: $C_{16}H_{19}FN_2 \cdot C_4H_4O_4 \cdot 0.50$ $C_2H_6O \cdot 0.50$ $H_2O$ Calc'd: C, 62.06; H, 6.70; N, 6.89. Found: C, 61.99; H, 6.61; N, 6.59.

EXAMPLE 25

8-Fluoro-3-methyl-2,3,4,5,9,10,11,12-octahydro-1H-[1,4]diazocino[7,8,1-jk]carbazole To a solution of 9-fluoro-4-methyl-3,4,5,6-tetrahydro-2H-benzo[e][1,4]diazocin-1-ylamine (1.79 g, 8.5 mmole) in 1-propanol (100 mL) was added cyclohexanone (9 ml, 86.8 mmole), followed by p-toluenesulfonic acid monohydrate (3.5 g, 18.1 mmole), and the resulting reaction mixture was refluxed for 30 hours. The reaction mixture was cooled to room temperature and solvent removed in vacuo to produce a brown residue. The residue was diluted with methylene chloride (300 mL) and washed with saturated aqueous sodium bicarbonate (200 mL), saturated aqueous sodium chloride (200 mL), dried (sodium sulfate) and concentrated in vacuo. Purification by flash column chromatography (silica gel, ethyl acetate:hexanes 1:1) provided 0.57 g of the title compound. 50 mg of the free amine was treated with one equivalent of fumaric acid in ethanol to form a fumarate salt 63.7 mg, mp 206–208° C. MS (ESI) m/z 273 ([M+H]$^+$).

Elemental Analysis for: $C_{17}H_{21}FN_2.C_4H_4O_4$ Calc'd: C, 64.93; H, 6.49; N, 7.21. Found: C, 64.98; H, 6.46; N, 6.95.

EXAMPLE 26

8-Fluoro-3-methyl-2,3,4,5,9,10,11,11a-octahydro-1H,8bH-cyclopenta[b][1,4]diazocino[7,8,1-hi]indole To a solution of 8-fluoro-3-methyl-2,3,4,5,10,11-hexahydro-1H,9H-cyclopenta[b][1,4]diazocino[7,8,1-hi]indole (0.23 g, 0.89 mmole) in acetic acid (50 mL) was added sodium cyanoborohydride (95 wt. %, 0.20 g, 3.02 mmole) and the reaction mixture was stirred at room temperature overnight. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% methanol in methylene chloride) provided 0.11 g of the title compound as a colorless oil. The oil was further treated with one equivalent of fumaric acid in ethanol to form a fumarate salt, mp 180–182° C. MS (ES) m/z 261.13 ([M+H]$^+$).

Elemental Analysis for: $C_{16}H_{21}FN_2.C_4H_4O_4$ Calc'd: C, 63.82; H, 6.69; N, 7.44. Found: C, 63.69; H, 6.52; N, 7.31.

EXAMPLE 27

8-Fluoro-3-methyl-2,3,4,5,8b,9,10,11,12,12a-decahydro-1H-[1,4]diazocino[7,8,1-jk]carbazole To a solution of 8-fluoro-3-methyl-2,3,4,5,9,10,11,12-octahydro-1H-[1,4]diazocino[7,8,1-jk]carbazole (0.12 g, 0.44 mmole) in acetic acid (50 mL) was added sodium cyanoborohydride (0.12 g, 1.76 mmole) and the reaction mixture was stirred at room temperature for 4 hours. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% methanol in methylene chloride) provided 60.0 mg of the title compound as a colorless oil. The oil was further treated with one equivalent of fumaric acid in ethanol to form a fumarate salt, mp 168–170° C. MS (ESI) m/z 275 ([M+H]$^+$).

Elemental Analysis for: $C_{17}H_{23}FN_2.C_4H_4O_4$ Calc'd: C, 64.60; H, 6.97; N, 7.17. Found: C, 64.64; H, 7.09; N, 7.07.

EXAMPLE 28

8-Fluoro-2,3,4,5,10,11-hexahydro-1H,9H-cyclopenta[b][1,4]diazocino[7,8,1-hi]indole To a solution of 8-fluoro-3-methyl-2,3,4,5,10,11-hexahydro-1H,9H-cyclopenta[b][1,4]diazocino[7,8,1-hi]indole (0.90 g, 3.48 mmole) in dichloroethane (200 mL) was added 1-chloroethyl chloroformate (1.5 mL, 13.8 mmole) and the mixture refluxed for 24 hours. The reaction mixture was then cooled to room temperature and the solvent removed in vacuo and replaced with methanol (200 mL) and refluxed for another 3 h. The reaction mixture was cooled to room temperature and the solvent removed in vacuo. The dark residue was dissolved in methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 3% methanol in dichloromethane) provided 0.59 g of the title compound as a white solid. 0.18 g of the above solid was further treated with one equivalent of fumaric acid in ethanol to form a fumarate salt, mp 199–200° C. MS (ES) m/z 245.11 ([M+H]$^+$), MS (ES) m/z 286.14 ([M+ACN+H]$^+$).

Elemental Analysis for: $C_{15}H_{17}FN_2.0.50\ C_4H_4O_4.0.25\ C_2H_6O$ Calc'd: C, 66.97; H, 6.58; N, 8.93. Found: C, 66.84; H, 6.32; N, 8.93.

EXAMPLE 29

8-Fluoro-2,3,4,5,9,10,11,12-octahydro-1H-[1,4]diazocino[7,8,1-jk]carbazole

To a solution of 8-fluoro-3-methyl-2,3,4,5,9,10,11,12-octahydro-1H-[1,4]diazocino[7,8,1-jk]carbazole (0.37 g, 3.48 mmole) in dichloroethane (100 mL) was added 1-chloroethyl chloroformate (1.0 mL, 9.18 mmole) and the mixture refluxed for 24 hours. The reaction mixture was cooled to room temperature and the solvent removed in vacuo and replaced with methanol (100 mL) and refluxed for another 3 hours. The reaction mixture was then cooled to room temperature and the solvent removed in vacuo. The dark residue was dissolved in methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 3% methanol in dichloromethane) provided 0.27 g of the title compound. 0.23 g of the above solid was further treated with one equivalent of fumaric acid in ethanol to form a fumarate salt, mp 177–179° C. MS (ESI) m/z 259 ([M+H]$^+$).

Elemental Analysis for: $C_{16}H_{19}FN_2.C_4H_4O_4.0.50\ C_2H_6O.0.30\ H_2O$ Calc'd: C, 62.61; H, 6.66; N, 6.95. Found: C, 62.60; H, 6.47; N, 6.73.

EXAMPLE 30

8-Fluoro-2,3,4,5,9,10,11,11a-octahydro-1H,8bH-cyclopenta[b][1,4]diazocino[7,8,1-hi]indole To a solution of 8-fluoro-2,3,4,5,10,11-hexahydro-1H,9H-cyclopenta[b][1,4]diazocino[7,8,1-hi]indole (0.41 g, 1.68 mmole) in acetic acid (50 mL) was added sodium cyanoborohydride (0.33 g, 4.99 mmole) and the reaction mixture was stirred at room temperature overnight. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 5% methanol in methylene chloride) provided 0.35 g of the title compound as a colorless oil. The oil was further treated with one equivalent of fumaric acid in ethanol to form a fumarate salt, mp 169–170° C. MS (ES) m/z 247.13 ([M+H]$^+$).

Elemental Analysis for: $C_{15}H_{19}FN_2.C_4H_4O_4$ Calc'd: C, 62.97; H, 6.40; N, 7.73. Found: C, 62.69; H, 6.24; N, 7.59.

EXAMPLE 31

8-Fluoro-2,3,4,5,8b,9,10,11,12,12a-decahydro-1H[1,4]diazocino[7,8,1-jk]carbazole To a solution of 8-fluoro-2,3,4,5,9,10,11,12-octahydro-1H-[1,4]diazocino[7,8,1-jk]carbazole (0.30 g, 1.16 mmole) in acetic acid (50 mL) was added sodium cyanoborohydride (0.22 g, 3.32 mmole) and the reaction mixture was stirred at room temperature for 4 hours. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 5% methanol in methylene chloride) provided 0.23 g of the title compound as a colorless oil. The oil was further treated with one equivalent of fumaric acid in ethanol to form a fumarate salt, mp 189–190° C. MS (ESI) m/z 261 ([M+H]$^+$).

Elemental Analysis for: $C_{16}H_{21}FN_2.C_4H_4O_4$ Calc'd: C, 63.82; H, 6.69; N, 7.44. Found: C, 63.43; H, 6.85; N, 7.24.

EXAMPLE 32

(+)-(8bR*,12aR*)-8-Fluoro-2,3,4,5,8b,9,10,11,12,12a-decahydro-1H-[1,4]diazocino[7,8,1-jk]carbazole To a solution of 8-fluoro-2,3,4,5,8b,9,10,11,12,12a-decahydro-1H-[1,4]diazocino[7,8,1-jk]carbazole (2.0 g, 7.68 mmole) in methylene chloride (200 mL) was added diisopropylethylamine (1.98 g, 15.00 mmole) and benzylchloroformate (1.96 g, 11.50 mmole). The resulting reaction mixture was stirred at room temperature overnight. The mixture was washed with saturated sodium bicarbonate (150 mL) and saturated sodium chloride (150 mL), dried (sodium sulfate) and concentrated. Purification by flash column chromatography (silica gel, methylene chloride) provided 2.0 g of the corresponding Cbz compound as a colorless oil. Chiral HPLC separation of the Cbz compound (Chiralcel OJ, 7% water in methanol/DEA) provided two fractions. 0.44 g of fraction I was treated with hydrogen bromide (30% in acetic acid, 10 mL) at room temperature for 2.5 hours. The reaction mixture was concentrated in vacuo. The residue was diluted with methylene chloride (200 mL), washed with aqueous sodium hydroxide (1N, 100 mL), saturated sodium bicarbonate (150 mL) and saturated sodium chloride (150 mL), dried (sodium sulfate) and concentrated. Purification by flash column chromatography (silica gel, methylene chloride to 8% methanol in methylene chloride) provided 0.10 g of the title compound. The oil was treated with one equivalent of fumaric acid in ethanol to form a fumarate salt (0.090 g, mp>130° C.). $[\alpha]_D^{25}$=+51.49° (c=4.46 mg/0.7 mL, MeOH). MS (EI) m/z 260(M+).

Elemental Analysis for: $C_{16}H_{21}FN_2.C_4H_4O_4.0.40$ $H_2O$ Calc'd: C, 62.62; H, 6.78; N, 7.30. Found: C, 62.88; H, 6.93; N, 7.15.

EXAMPLE 33

(−)-(8bR*,12aR*)-8-Fluoro-2,3,4,5,8b,9,10,11,12,12a-decahydro-1H-[1,4]diazocino[7,8,1-jk]carbazole 0.62 g of fraction II from example 32 (chiral HPLC separation of the Cbz compound of 8-fluoro-2,3,4,5,8b,9,10,11,12,12a-decahydro-1H-[1,4]diazocino[7,8,1-jk]carbazole) was treated with hydrogen bromide (30% in acetic acid, 10 mL) at room temperature for 2.5 hours. The reaction mixture was concentrated in vacuo. The residue was diluted with methylene chloride (200 mL), washed with aqueous sodium hydroxide (1N, 100 mL), saturated sodium bicarbonate (150 mL) and saturated sodium chloride (150 mL), dried (sodium sulfate) and concentrated. Purification by flash column chromatography (silica gel, methylene chloride to 8% methanol in methylene chloride) provided 0.18 g of the title compound. This was treated with one equivalent of fumaric acid in ethanol to form a fumarate salt 0.21 g, mp 94–96° C. $[\alpha]_D^{25}$=−56.10° (c=0.82% solution in MeOH). MS (ES) m/z 261.11 ([M+H]$^+$).

Elemental Analysis for: $C_{16}H_{21}FN_2.0.18$ $CH_2Cl_2$ Calc'd: C, 70.50; H, 7.81; N, 10.16. Found: C, 70.53; H, 8.11; N, 10.02.

Intermediate 18

2-(4-Chloro-2-nitro-phenyl)-ethanol (known Compound 16764-17-3)

To a solution of 4-chloro-1-methyl-2-nitro-benzene (171.6 g, 0.5 mole) in DMSO (150 mL) was added paraformaldehyde (30.0 g, 1.0 mole), followed by potassium hydroxide (1.5 g, 0.027 mol) in ethanol (10 mL). The resulting reaction mixture was stirred at room temperature for six days and water (2 L) was added and the mixture neutralized with hydrochloric acid (2 N). The mixture was extracted with ethyl ether (2×1 L) and the combined organic layers were washed with water (1 L), saturated sodium chloride (1 L), dried (sodium sulfate) and concentrated to a yellow solid. Purification by flash column chromatography (silica gel, methylene chloride:hexanes 1:2) provided 63.0 g of the title compound as a yellow solid. $^1$H NMR (DMSO-d$_6$): 7.90 δ (s, 1H); 7.50 δ (d, 1H); 7.36 δ (d, 1H); 3.90 δ (t, 2H); 3.15 δ (t, 2H); 1.50 δ (broad, 1H).

Intermediate 19

1-(2-Bromo-ethyl)-4-chloro-2-nitro-benzene

To a solution of 2-(4-chloro-2-nitro-phenyl)-ethanol (63.0 g, 0.31 mole) in methylene chloride (1 L) was added triphenylphosphine (81.9 g, 0.31 mole) and the mixture was cooled to 0° C. Carbon tetrabromide (103.6 g, 0.31 mole) in methylene chloride (100 mL) was added dropwise through an addition funnel. The reaction mixture was stirred at room temperature overnight. The solvent was removed in vacuo and the residue purified by flash column chromatography (silica gel, dichloromethane) to provide 78.0 g of the title compound as a light brown oil.

$^1$H NMR (CDCl$_3$): 8.00 δ (s, 1H); 7.58 δ (d, 1H); 7.38 δ (d, 1H); 3.605 δ (t, 2H); 3.45 δ (t, 2H).

Intermediate 20

[2-(4-Chloro-2-nitro-phenyl)-ethyl]-methyl-amine

To a solution of methyl amine in THF (2 M, 200 mL) was added 1-(2-bromo-ethyl)-4-chloro-2-nitro-benzene (17.5 g, 0.066 mole) in a pressure bottle, the reaction mixture was stirred at 60° C. overnight and the solvent was removed. The solid residue was treated with sodium hydroxide (1 N, 100 mL) and the aqueous extracted with methylene chloride (2×100 mL). The combined organic layers were washed with water (100 mL), saturated sodium chloride (100 mL), dried (sodium sulfate) and concentrated to provide 14.9 g of the title compound as a brown oil. $^1$H NMR (DMSO-d$_6$): 7.95 δ (d, 1H); 7.67 δ (dd, 1H); 7.50 δ (t, 1H); 3.28 δ (broad, 1H); 2.85 δ (t, 2H); 2.64 δ (t, 2H); 2.20 δ (s, 3H).

Intermediate 21

{[2-(4-Chloro-2-nitro-phenyl)-ethyl]-methyl-amino}-acetic acid ethyl ester

A solution of [2-(4-chloro-2-nitro-phenyl)-ethyl]-methyl-amine (29.8 g, 0.14 mole) and ethyl bromoacetate (23.2 g, 0.14 mole) in acetonitrile (500 mL) containing potassium carbonate (9.6 g, 0.07 mole) was stirred at room temperature overnight. The mixture was evaporated in vacuo, water was added to the residue and then extracted with dichloromethane (2×200 mL). The combined organic layers were washed with saturated sodium chloride (300 mL), dried and concentrated. Purification by flash column chromatography (silica gel, methylene chloride) provided 22.5 g of the title compound as a brown oil. $^1$H NMR (DMSO): 7.98 δ (d, 1H); 7.68 δ (dd, 1H); 7.52 δ (d, 1H); 4.00 δ (m, 2H); 3.20 δ (s, 2H); 2.88 δ (t, 2H); 2.68 δ (t, 2H); 2.25 δ (s, 3H); 1.10 δ (t, 3H).

Intermediate 22

{[2-(4-chloro-2-nitro-phenyl)-ethyl]-methyl-amino}-acetic acid

{[2-(4-Chloro-2-nitro-phenyl)-ethyl]-methyl-amino}-acetic acid ethyl ester (22.5 g, 0.075 mole) dissolved in concentrated hydrobromic acid (48 wt. % in water, 200 mL) was allowed to stir at 70° C. overnight and then reduced to a small volume in vacuo. The residue oil was taken up in acetonitrile and the solution was evaporated in vacuo. This procedure was repeated until the water was removed and a crystalline residue remained. This material (18.5 g) was used in the next step without further purification.

Intermediate 23

9-Chloro-4-methyl-3,4,5,6-tetrahydro-1H-benzo[e][1,4]diazocin-2-one

{[2-(4-Chloro-2-nitro-phenyl)-ethyl]-methyl-amino}-acetic acid (18.5 g, approximately 0.068 mole, not quite pure) in methanol (250 mL) containing platinum on sulfided carbon (5 wt. %, 12.0 g) was hydrogenated at room temperature and a hydrogen pressure of 50 psi overnight. The catalyst was removed by filtration through Celite and the filtrate was evaporated to dryness in vacuo. The residue was dissolved in pyridine (2 L) and the solution was cooled to 0° C., and 1,3-dicyclohexylcarbodiimide (30.0 g, 0.145 mol) was added. The reaction mixture was allowed to warm up to room temperature and stirred at room temperature for 48 hours. The solvent was removed and the residue was slurried with 10% hydrochloric acid and filtered. The filtrate was extracted with ether, the aqueous phase was made basic with sodium carbonate and then extracted with dichloromethane. The extract was dried over sodium sulfate and evaporated in vacuo. Purification by flash column chromatography (silica gel, methylene chloride) provided 5.1 g of the title compound as a white solid. $^1$H NMR (CDCl$_3$): 7.55 δ (broad s, 1H); 7.18 δ (d, 1H); 7.10 δ (d, 1H); 7.00 δ (s, 1H); 3.18 δ (s, 2H); 2.80 δ (broad s, 4H); 2.40 δ (s, 3H).

Intermediate 24

9-Chloro-4-methyl-1,2,3,4,5,6-hexahydro-benzo[e][1,4]diazocine

A solution of the lactam 9-chloro-4-methyl-3,4,5,6-tetrahydro-1H-benzo[e][1,4]diazocin-2-one (5.1 g, 0.023 mole) in THF (100 mL) was added dropwise to a stirred suspension of lithium aluminum hydride (3.0 g, 0.075 mole) in THF (200 mL). The resulting mixture was stirred at reflux for 3 hours and the excess hydride was destroyed at 0° C. by the cautious addition of ethyl acetate. The mixture was washed with aqueous potassium sodium tartrate (10% v/w, 200 mL) and saturated aqueous sodium chloride (150 mL), dried (sodium sulfate) and concentrated. Evaporation of in vacuo provided 6.0 g of the title compound as a light yellow oil with minor impurities.

Intermediate 25

9-Chloro-4-methyl-3,4,5,6-tetrahydro-2H-benzo[e][1,4]diazocin-1-ylamine

To a solution of 9-chloro-4-methyl-1,2,3,4,5,6-hexahydro-benzo[e][1,4]diazocine (6.0 g, 0.023 mole approximately) in hydrochloric acid (1 N, 200 mL) cooled to 0° C. was added sodium nitrite (4.0 g, 0.058 mole) in water (20 mL). The mixture was stirred for 1 hour and treated with sodium bicarbonate, extracted with ethyl acetate (3×100 mL). The combined organic layers were washed with saturated sodium chloride (200 mL), dried and concentrated to a light brown oil. The oil was redissolved in THF (50 mL) and added to a suspension of lithium aluminum hydride (4.0 g, 0.10 mole) in THF (100 mL) and the mixture refluxed for 3 hours. The excess hydride was destroyed at 0° C. by the cautious addition of ethyl acetate. The mixture was washed with aqueous potassium sodium tartrate (10% v/w, 200 mL) and saturated aqueous sodium chloride (150 mL), dried (sodium sulfate) and concentrated. Evaporation in vacuo provided 4.9 g of the title compound as a light yellow oil. This oil was used for indole formation without further purification. $^1$H NMR (CDCl$_3$): 7.25 δ (s, 1H); 7.00 δ (d, 2H); 3.00 δ (m, 2H); 2.90 δ (m, 2H); 2.78 δ (m, 2H); 2.40 δ (s, 3H); 2.30 δ (t, 2H).

EXAMPLE 34

8-Chloro-3-methyl-2,3,4,5,10,11-hexahydro-1H,9H-cyclopenta[b][1,4]diazocino[7,8,1-hi]indole To a solution of 9-chloro-4-methyl-3,4,5,6-tetrahydro-2H-benzo[e][1,4]diazocin-1-ylamine (3.5 g, 15.5 mmole) in 1-propanol (200 mL) was added cyclopentanone (20.0 ml, 226.1 mmole), followed by p-toluenesulfonic acid monohydrate (11.0 g, 57.8 mmole), and the resulting reaction mixture was refluxed for 30 hours. The reaction mixture was cooled to room temperature and solvent removed in vacuo to produce a brown residue. The residue was diluted with methylene chloride (300 mL) and washed with saturated aqueous sodium bicarbonate (200 mL), saturated aqueous sodium chloride (200 mL), dried (sodium sulfate) and concentrated in vacuo. Purification by flash column chromatography (silica gel, ethyl acetate:hexanes 1:1) provided 1.3 g of the title compound. 0.11 g of the free amine was treated with one equivalent of fumaric acid in ethanol to form a fumarate salt (0.12 g, mp 209–211° C.). MS (ES) m/z 275.1 ([M+H]$^+$).

Elemental Analysis for: C$_{16}$H$_{19}$ClN$_2$.C$_4$H$_4$O$_4$ Calc'd: C, 61.46; H, 5.93; N, 7.17. Found: C, 61.31; H, 5.86; N, 7.00.

EXAMPLE 35

8-Chloro-3-methyl-2,3,4,5,9,10,11,12-octahydro-1H-[1,4]diazocino[7,8,1-jk]carbazole To a solution of 9-chloro-4-methyl-3,4,5,6-tetrahydro-2H-benzo[e][1,4]diazocin-1-ylamine (4.9 g, 22.0 mmole) in 1-propanol (300 mL) was added cyclohexanone (25.0 ml, 240.0 mmole), followed by p-toluenesulfonic acid monohydrate (10.0 g, 50.0 mmole), and the resulting reaction mixture was refluxed for 30 hours. The reaction mixture was cooled to room temperature and solvent removed in vacuo to produce a brown residue. The residue was diluted with methylene chloride (300 mL) and washed with saturated aqueous sodium bicarbonate (200 mL), saturated aqueous sodium chloride (200 mL), dried (sodium sulfate) and concentrated in vacuo. Purification by flash column chromatography (silica gel, ethyl acetate:hexanes 1:1) provided 3.05 g of the title compound. 0.335 g of the free amine was treated with one equivalent of fumaric acid in ethanol to form a fumarate salt (0.544 g, mp 212–214° C.). MS (ES) m/z 289 ([M+H]$^+$).

Elemental Analysis for: $C_{17}H_{21}ClN_2 \cdot C_4H_4O_4 \cdot 0.30$ $H_2O$ Calc'd: C, 61.48; H, 6.29; N, 6.83. Found: C, 61.46; H, 6.28; N, 6.75.

EXAMPLE 36

8-Chloro-3-methyl-2,3,4,5,9,10,11,11a-octahydro-1H,8bH-cyclopenta[b][1,4]diazocino[7,8,1-hi]indole To a solution of 8-chloro-3-methyl-2,3,4,5,10,11-hexahydro-1H,9H-cyclopenta[b][1,4]diazocino[7,8,1-hi]indole (0.20 g, 0.73 mmole) in acetic acid (50 mL) was added sodium cyanoborohydride (0.45 g, 6.80 mmole) and the reaction mixture was stirred at room temperature for 2 hours. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% methanol in methylene chloride) provided 0.13 g of the title compound as a colorless oil. The oil was further treated with one equivalent of fumaric acid in ethanol to form a fumarate salt, mp 179–181° C. MS (ES) m/z 277.10 ([M+H]$^+$).

Elemental Analysis for: $C_{16}H_{21}ClN_2 \cdot C_4H_4O_4$ Calc'd: C, 61.14; H, 6.41; N, 7.13. Found: C, 61.24; H, 6.81; N, 6.99.

EXAMPLE 37

8-Chloro-3-methyl-2,3,4,5,8b,9,10,11,12,12a-decahydro-1H-[1,4]diazocino[7,8,1-jk]carbazole To a solution of 8-chloro-3-methyl-2,3,4,5,9,10,11,12-octahydro-1H-[1,4]diazocino[7,8,1-jk]carbazole (0.25 g, 0.86 mmole) in acetic acid (50 mL) was added sodium cyanoborohydride (0.22 g, 3.32 mmole) and the reaction mixture was stirred at room temperature overnight. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% methanol in methylene chloride) provided 80 mg of the title compound as a colorless oil. The oil was further treated with one equivalent of fumaric acid in ethanol to form a fumarate salt, mp 178–180° C. MS (ESI) m/z 291 ([M+H]$^+$).

Elemental Analysis for: $C_{17}H_{23}ClN_2 \cdot C_4H_4O_4$ Calc'd: C, 61.99; H, 6.69; N, 6.88. Found: C, 61.80; H, 6.70; N, 6.75.

EXAMPLE 38

8-Chloro-2,3,4,5,10,11-hexahydro-1H,9H-cyclopenta[b][1,4]diazocino[7,8,1-hi]indole To a solution of 8-chloro-3-methyl-2,3,4,5,10,11-hexahydro-1H,9H-cyclopenta[b][1,4]diazocino[7,8,1-hi]indole (1.0 g, 3.64 mmole) in dichloroethane (200 mL) was added 1-chloroethyl chloroformate (2.0 mL, 18.35 mmole) and refluxed for 24 hours. The reaction mixture was cooled to room temperature and the solvent removed in vacuo and replaced with methanol (200 mL) and refluxed for another 3 hours. The reaction mixture was cooled to room temperature and the solvent removed in vacuo. The dark residue was dissolved in methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 3% methanol in dichloromethane) provided 0.70 g of the title compound as a white solid. 0.12 g of the above solid was further treated with one equivalent of fumaric acid in ethanol to form a fumarate salt, mp 226–228° C. MS (ES) m/z 261.09 ([M+H]$^+$), MS (ES) m/z 302.12 ([M+ACN+H]$^+$).

Elemental Analysis for: $C_{15}H_{17}ClN_2 \cdot 0.50$ $C_4H_4O_4$ Calc'd: C, 64.05; H, 6.01; N, 8.79. Found: C, 63.74; H, 6.04; N, 8.53.

EXAMPLE 39

8-Chloro-2,3,4,5,9,10,11,12-octahydro-1H-[1,4]diazocino[7,8,1-jk]carbazole

To a solution of 8-chloro-3-methyl-2,3,4,5,9,10,11,12-octahydro-1H-[1,4]diazocino[7,8,1-jk]carbazole (0.60 g, 2.08 mmole) in dichloroethane (100 mL) was added 1-chloroethyl chloroformate (1.5 mL, 13.76 mmole) and refluxed for 24 hours. The reaction mixture was cooled to room temperature and the solvent removed in vacuo and replaced with methanol (100 mL) and refluxed for another 3 hours. The reaction mixture was cooled to room temperature and the solvent removed in vacuo. The dark residue was dissolved in methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 3% methanol in dichloromethane) provided 0.58 g of the title compound. This solid was further treated with one equivalent of fumaric acid in ethanol to form a fumarate salt, mp 199–201° C. MS (ES) m/z 275.10 ([M+H]$^+$), MS (ES) m/z 316.13 ([M+ACN+H]$^+$).

Elemental Analysis for: $C_{16}H_{19}ClN_2 \cdot 0.50$ $C_4H_4O_4$ Calc'd: C, 64.96; H, 6.36; N, 8.42. Found: C, 64.80; H, 6.28; N, 8.31.

EXAMPLE 40

8-Chloro-2,3,4,5,9,10,11,11a-octahydro-1H,8bH-cyclopenta[b][1,4]diazocino[7,8,1-hi]indole To a solution of 8-chloro-2,3,4,5,10,11-hexahydro-1H,9H-cyclopenta[b][1,4]diazocino[7,8,1-hi]indole (0.60 g, 2.30 mmole) in acetic acid (100 mL) was added sodium cyanoborohydride (0.60 g, 9.07 mmole) and the reaction mixture was stirred at room temperature overnight. The solvent was removed in vacuo and the residue was diluted with methylene chloride (200 mL) and washed with aqueous sodium hydroxide (1N, 150 mL), saturated sodium chloride (150 mL), dried (sodium sulfate) and concentrated. Purification by flash column chromatography (silica gel, 1.5% to 5% methanol in methylene chloride) provided 0.30 g of the title compound as a white solid. 60 mg of this compound was further treated with one equivalent of fumaric acid in ethanol to form a fumarate salt, mp 169–170° C. MS (ES) m/z 263.1 ([M+H]$^+$), MS (ES) m/z 304.1 ([M+ACN+H]$^+$).

Elemental Analysis for: $C_{15}H_{19}ClN_2$ $C_4H_4O_4 \cdot 0.30$ $C_2H_6O$ Calc'd: C, 59.95; H, 6.37; N, 7.13. Found: C, 59.95; H, 6.54; N, 7.17.

EXAMPLE 41

8-Chloro-2,3,4,5,8b,9,10,11,12,12a-decahydro-1H-[1,4]diazocino[7,8,1-jk]carbazole To a solution of 8-chloro-2,3,4,5,9,10,11,12-octahydro-1H-[1,4]diazocino[7,8,1-jk]carbazole (2.2 g, 8.00 mmole) in acetic acid (200 mL) was added sodium cyanoborohydride (95 wt. %, 2.5 g, 40.0 mmole) and the reaction mixture was stirred at room temperature overnight. The solvent was removed in vacuo and the residue was diluted with methylene chloride (400 mL) and washed with aqueous sodium hydroxide (1N, 300 mL), saturated sodium chloride (300 mL), dried (sodium sulfate) and concentrated. Purification by flash column chromatography (silica gel, 1.5% to 5% methanol in methylene chloride) provided 1.67 g of the title compound. 0.116 g of the compound was further treated with one equivalent of fumaric acid in ethanol to form a fumarate salt, mp 199–200° C. MS (ES) m/z 277.1 ([M+H]$^+$).

Elemental Analysis for: $C_{16}H_{21}ClN_2.C_4H_4O_4$ Calc'd: C, 61.14; H, 6.41; N, 7.13. Found: C, 60.86; H, 6.43; N, 6.99.

EXAMPLE 42

(+)-(8bR*,12aR*)-8-Chloro-2,3,4,5,8b,9,10,11,12, 12a-decahydro-1H-[1,4]diazocino[7,8,1-jk]carbazole To a solution of 8-chloro-2,3,4,5,8b,9,10,11,12,12a-decahydro-1H-[1,4]diazocino[7,8,1-jk]carbazole (1.55 g, 5.60 mmole) in methylene chloride (200 mL) was added diisopropylethylamine (1.80 g, 14.00 mmole) and benzylchloroformate (1.43 g, 8.40 mmole). The resulting reaction mixture was stirred at room temperature 4 hours. The mixture was washed with saturated sodium bicarbonate (150 mL) and saturated sodium chloride (150 mL), dried (sodium sulfate) and concentrated. Purification by flash column chromatography (silica gel, methylene chloride) provided 2.3 g of the corresponding Cbz compound as a colorless oil. Chiral HPLC separation of the Cbz compound (Chiralcel OJ, 7% water in methanol/DEA) provided two fractions. 0.53 g of fraction I was treated with hydrogen bromide (30% in acetic acid, 15 mL) at room temperature for 2.5 hours. The reaction mixture was concentrated in vacuo. The residue was washed thoroughly with diethyl ether and then diluted with methylene chloride (200 mL), washed saturated sodium bicarbonate (150 mL) and saturated sodium chloride (150 mL), dried (sodium sulfate) and concentrated. Purification by flash column chromatography (silica gel, methylene chloride to 8% methanol in methylene chloride) provided 0.32 g of the title compound. This was treated with one equivalent of fumaric acid in ethanol to form a fumarate salt (0.24 g, mp 170–173° C.). $[\alpha]_D^{25}$=+8.95 (c=0.92%, MeOH). MS (EI) m/z 277(M+).

Elemental Analysis for: $C_{16}H_{21}ClN_2.C_4H_4O_4$ Calc'd: C, 61.14; H, 6.41; N, 7.13. Found: C, 61.16; H, 6.41; N, 6.91.

EXAMPLE 43

(−)-(8bR*,12aR*)-8-Chloro-2,3,4,5,8b,9,10,11,12, 12a-decahydro-1H-[1,4]diazocino[7,8,1-jk]carbazole 0.58 g of fraction II from example 42 (chiral HPLC separation of the Cbz compound of 8-chloro-2,3,4,5,8b,9, 10,11,12,12a-decahydro-1H-[1,4]diazocino[7,8,1-jk] carbazole) was treated with hydrogen bromide (30% in acetic acid, 15 mL) at room temperature for 2.5 hours. The reaction mixture was concentrated in vacuo. The residue was washed thoroughly with diethyl ether and then diluted with methylene chloride (200 mL), washed saturated sodium bicarbonate (150 mL) and saturated sodium chloride (150 mL), dried (sodium sulfate) and concentrated. Purification by flash column chromatography (silica gel, methylene chloride to 8% methanol in methylene chloride) provided 0.26 g of the title compound. This was treated with one equivalent of fumaric acid in ethanol to form a fumarate salt (0.18 g, mp 168–171° C.). $[\alpha]_D^{25}$=−9.53° (c=0.86% solution in MeOH). MS (ES) m/z 277.1 ([M+H]$^+$).

Elemental Analysis for: $C_{16}H_{21}ClN_2.C_4H_4O_4$.0.20 $H_2O$ Calc'd: C, 60.59; H, 6.46; N, 7.07. Found: C, 60.61; H, 6.39; N, 6.91.

EXAMPLE 44

3-Methyl-2,3,4,5,9,10,11,12-octahydro-1H,9H-[1,4] diazocino[7,8,1-hi]thiopyrano[4,3-b]indole To a solution of 3-methyl-2,3,4,5,11,12-hexahydro-1H, 9H-[1,4]diazocino[7,8,1-hi]thiopyrano[4,3-b]indole (0.10 g, 0.37 mmole) in acetic acid (50 mL) was added sodium cyanoborohydride (0.10 g, 1.51 mmole) and the reaction mixture was stirred at room temperature for 5 h. The solvent was removed in vacuo and the residue was diluted with ethyl acetate (300 mL) and washed with saturated sodium bicarbonate (150 mL), saturated sodium chloride (150 mL), dried (sodium sulfate) and concentrated. Purification by flash column chromatography (silica gel, ethyl acetate:hexanes 3:2) provided 26 mg of the title compound. This was further treated with one equivalent of fumaric acid in ethanol to form a fumarate salt, mp 187–9° C. MS (ESI) m/z 275 ([M+H]+).

Elemental Analysis for: $C_{16}H_{22}N_2S.C_4H_4O_4$ Calc'd: C, 61.52; H, 6.71; N, 7.17. Found: C, 61.35; H, 6.69; N, 7.14.

EXAMPLE 45

(+)-(8bR*,11aR*)-2,3,4,5,9,10,11,11a-Octahydro-1H,8bH-cyclopenta[b][1,4]diazocino[7,8,1-hi]indole To a solution of 2,3,4,5,9,10,11,11a-octahydro-1H,8bH-cyclopenta[b][1,4]diazocino[7,8,1-hi]indole (2.10 g, 9.21 mmole) in methylene chloride (250 mL) was added diisopropylethylamine (2.38 g, 18.42 mmole) and benzylchloroformate (2.36 g, 13.8 mmole). The resulting reaction mixture was stirred at room temperature for 3 hours. The mixture was washed with saturated sodium bicarbonate (200 mL) and saturated sodium chloride (200 mL), dried (sodium sulfate) and concentrated. Purification by flash column chromatography (silica gel, methylene chloride) provided 3.17 g of the corresponding Cbz compound. Chiral HPLC separation of the Cbz compound (Chiralpak AD, ethanol) provided two fractions. To a solution of 1.0 g of fraction I in methanol (100 mL) was added palladium on carbon (5 wt. %, 0.22 g) and the reaction mixture was shaken under a hydrogen atmosphere (50 psi) for 5 hours. The reaction mixture was filtered (celite) and the solvent removed in vacuo to provide 0.53 g of light yellow oil. The oil was treated with hydrogen chloride (1.0 N in diethyl ether, 5 mL). The resulting precipitate was filtered, washed (diethyl ether), and dried to afford 0.53 g of the title compound as a white solid, hydrochloride salt, mp>130° C. $[\alpha]_D^{25}$=+57.4° (c=1%, MeOH). MS (ES) m/z 229.1 ([M+H]$^+$).

Elemental Analysis for: $C_{15}H_{20}N_2$.2.00 HCl Calc'd: C, 59.80; H, 7.36; N, 9.30. Found: C, 60.07; H, 7.91; N, 9.11.

EXAMPLE 46

(−)-(8bR*,11aR*)-2,3,4,5,9,10,11,11a-Octahydro-1H,8bH-cyclopenta[b][1,4]diazocino[7,8,1-hi]indole To a solution of 1.1 g of fraction II from example 45 (chiral HPLC separation of the Cbz compound of 2,3,4,5, 9,10,11,11a-octahydro-1H,8bH-cyclopenta[b][1,4] diazocino[7,8,1-hi]indole) in methanol (100 mL) was added palladium on carbon (5 wt. %, 0.25 g) and the reaction mixture was shaken under a hydrogen atmosphere (50 psi) for 5 hours. The reaction mixture was filtered (celite) and the solvent removed in vacuo to provide 0.66 g of light yellow oil. The oil was treated with hydrogen chloride (1.0 N in diethyl ether, 5 mL). The resulting precipitate was filtered, washed (diethyl ether), and dried to afford 0.64 g of the title compound as a white solid, hydrochloride salt, mp>130° C. $[\alpha]_D^{25}$=−54.2° (c=1%, MeOH). MS (ES) m/z 229.1 ([M+H]$^+$).

Elemental Analysis for: $C_{15}H_{20}N_2 \cdot 1.50$ HCl Calc'd: C, 63.66; H, 7.66; N, 9.90. Found: C, 63.36; H, 7.86; N, 9.61.

EXAMPLE 47

(+)-(8bR*,12aR*)-2,3,4,5,8b,9,10,11,12,12a-Decahydro-1H-[1,4]diazocino[7,8,1-jk]carbazole To a solution of 2,3,4,5,8b,9,10,11,12,12a-decahydro-1H-[1,4]diazocino[7,8,1jk]carbazole (0.95 g, 3.9 mmole) in methylene chloride (100 mL) was added diisopropylethylamine (1.27 g, 9.80 mmole) and benzylchloroformate (1.00 g, 5.85 mmole). The resulting reaction mixture was stirred at room temperature overnight. The mixture was washed with saturated sodium bicarbonate (100 mL) and saturated sodium chloride (100 mL), dried (sodium sulfate) and concentrated. Purification by flash column chromatography (silica gel, methylene chloride) provided the corresponding Cbz compound. Chiral HPLC separation of the Cbz compound (Chiralcel AD, 8:2 hexane:isopropanol) provided two fractions. To a solution of 0.24 g of fraction I in methanol (100 mL) was added palladium on carbon (5 wt. %, 0.10 g) and the reaction mixture was shaken under a hydrogen atmosphere (50 psi) for 5 hours. The reaction mixture was filtered (celite) and the solvent removed in vacuo to provide 0.14 g of light yellow oil. The oil was treated with one equivalent of fumaric acid in ethanol to form a fumarate salt 0.126 g, mp 139–140° C. $[\alpha]_D^{25}$=+55.40° (c=1% solution in MeOH). MS (ES) m/z 243.1 ([M+H]$^+$).

Elemental Analysis for: $C_{16}H_{22}N_2 \cdot C_4H_4O_4$ Calc'd: C, 67.02; H, 7.31; N, 7.82. Found: C, 66.65; H, 7.29; N, 7.66.

EXAMPLE 48

(−)-(8bR*,12aR*)-2,3,4,5,8b,9,10,11,12,12a-Decahydro-1H[1,4]diazocino[7,8,1-jk]carbazole To a solution of 0.20 g of fraction II from example 47 (chiral HPLC separation of the Cbz compound of 2,3,4,5,8b,9,10,11,12,12a-decahydro-1H-[1,4]diazocino[7,8,1-jk] carbazole) in methanol (100 mL) was added palladium on carbon (5 wt. %, 0.25 g) and the reaction mixture was shaken under a hydrogen atmosphere (50 psi) for 5 hours. The reaction mixture was filtered (celite) and the solvent removed in vacuo to provide 0.088 g of light yellow oil. The oil was treated with one equivalent of fumaric acid in ethanol to form a fumarate salt 0.087 g, mp 139–140° C. $[\alpha]_D^{25}$=−53.80° (c=1% solution in MeOH). MS (ES) m/z 243.1 ([M+H]$^+$).

Elemental Analysis for: $C_{16}H_{22}N_2 \cdot C_4H_4O_4 \cdot 0.20$ $H_2O$ Calc'd: C, 66.35; H, 7.35; N, 7.74. Found: C, 66.48; H, 7.25; N, 7.58.

What is claimed is:
1. A compound of Formula I:

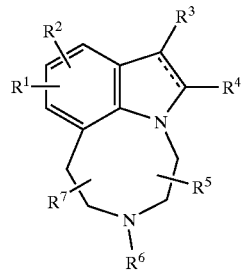

wherein
$R^1$ and $R^2$ are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;
$R^3$ and $R^4$ are, independently, hydrogen or alkyl of 1 to 6 carbon atoms, or $R^3$ and $R^4$, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sulfone, wherein the cyclic moiety may optionally be substituted with 1 to 3 alkyl moieties of 1 to 6 carbon atoms;
$R^5$, $R^6$ and $R^7$ are, independently, hydrogen or alkyl of 1 to 6 carbon atoms; and
a dotted line represents an optional double bond;
or a pharmaceutically acceptable salt thereof.
2. The compound of claim 1 wherein $R^1$ and $R^2$ are independently hydrogen, halo, cyano, trifluoromethyl, alkyl of 1 to 6 carbon atoms, alkoxy of 1 to 6 carbon atoms, alkanoyl of 2 to 6 carbon atoms or alkanesulfonyl of 1 to 6 carbon atoms.
3. The compound of claim 1 wherein $R^1$ and $R^2$ are independently hydrogen, halo, trifluoromethyl or alkyl of 1 to 3 carbon atoms.
4. The compound of claim 1 wherein $R^1$ is substituted at the 9-position of the [1,4]diazocino[7,8,1-hi]indole ring system of Formula I.
5. The compound of claim 1 wherein $R^3$ and $R^4$ are taken together with the carbon atoms to which they are attached to form a cycloalkane of 5 to 8 carbon atoms optionally substituted with 1 to 3 alkyl moieties of 1 to 3 carbon atoms, cycloalkene of 5 to 8 carbon atoms, optionally substituted with 1 to 3 alkyl moieties of 1 to 3 carbon atoms, pyran or thiopyran, in which the sulfur atom is optionally oxidized to a sulfoxide or sulfone.
6. The compound of claim 1 wherein $R^3$ and $R^4$ are taken together with the carbon atoms to which they are attached to form cycloalkane of 5 to 8 carbon atoms, cycloalkene of 5 to 8 carbon atoms or thiopyran.
7. The compound of claim 1 wherein $R^3$ and $R^4$ are taken together with the carbon atoms to which they are attached to form cyclopentane, cyclohexane or cyclohexene.
8. The compound of claim 1 wherein $R^5$ is hydrogen or alkyl of 1 to 3 carbon atoms.
9. The compound of claim 1 wherein $R^6$ is hydrogen or alkyl of 1 to 3 carbon atoms.

10. The compound of claim 1 wherein $R^7$ is hydrogen or alkyl of 1 to 3 carbon atoms.

11. The compound of claim 1 wherein $R^5$, $R^6$ and $R^7$ are each hydrogen.

12. The compound of claim 1 wherein $R^1$ and $R^2$ are independently selected from hydrogen, halo, trifluoromethyl or alkyl of 1 to 3 carbon atoms; $R^5$, $R^6$ and $R^7$ are each hydrogen; and $R^3$ and $R^4$, taken together with the carbon atoms to which they are attached, form cyclopentane, cyclohexane or cyclohexene.

13. The compound of claim 1 selected from:
    a) 3-methyl-2,3,4,5,10,11-hexahydro-1H,9H-cyclopenta[b][1,4]diazocino[7,8,1-hi]indole;
    b) 2,3,4,5,10,11-hexahydro-1H,9H-cyclopenta[b][1,4]diazocino[7,8,1-hi]indole;
    c) 3-methyl-2,3,4,5,9,10,11,11a-octahydro-1H,8bH-cyclopenta[b][1,4]diazocino[7,8,1-hi]indole;
    d) 2,3,4,5,9,10,11,11a-octahydro-1H,8bH-cyclopenta[b][1,4]diazocino[7,8,1-hi]indole;
    e) 6-chloro-3-methyl-2,3,4,5,10,11-hexahydro-1H,9H-cyclopenta[b][1,4]diazocino[7,8,1-hi]indole;
    f) 6-chloro-3-methyl-2,3,4,5,9,10,11,11a-octahydro-1H,8bH-cyclopenta[b][1,4]diazocino[7,8,1-hi]indole;
    g) 6-chloro-2,3,4,5,10,11-hexahydro-1H,9H-cyclopenta[b][1,4]diazocino[7,8,1-hi]indole;
    h) 6-chloro-2,3,4,5,9,10,11,11a-octahydro-1H,8bH-cyclopenta[b][1,4]diazocino[7,8,1-hi]indole;
    i) 6-chloro-3-ethyl-2,3,4,5,9,10,11,11a-octahydro-1H,8bH-cyclopenta[b][1,4]diazocino[7,8,1-hi]indole;
    j) 8-fluoro-3-methyl-2,3,4,5,10,11-hexahydro-1H,9H-cyclopenta[b][1,4]diazocino[7,8,1-hi]indole;
    k) 8-fluoro-3-methyl-2,3,4,5,9,10,11,11a-octahydro-1H,8bH-cyclopenta[b][1,4]diazocino[7,8,1-hi]indole;
    l) 8-fluoro-2,3,4,5,10,11-hexahydro-1H,9H-cyclopenta[b][1,4]diazocino[7,8,1-hi]indole;
    m) 8-fluoro-2,3,4,5,9,10,11,11a-octahydro-1H,8bH-cyclopenta[b][1,4]diazocino[7,8,1-hi]indole;
    n) 8-chloro-3-methyl-2,3,4,5,10,11-hexahydro-1H,9H-cyclopenta[b][1,4]diazocino[7,8,1-hi]indole;
    o) 8-chloro-3-methyl-2,3,4,5,9,10,11,11a-octahydro-1H,8bH-cyclopenta[b][1,4]diazocino[7,8,1-hi]indole;
    p) 8-chloro-2,3,4,5,10,11-hexahydro-1H,9H-cyclopenta[b][1,4]diazocino[7,8,1-hi]indole; or
    q) 8-chloro-2,3,4,5,9,10,11,11a-octahydro-1H,8bH-cyclopenta[b][1,4]diazocino[7,8,1-hi]indole;
    or a pharmaceutically acceptable salt thereof.

14. The compound of claim 13 selected from:
    (+)-(8bR*,11aR*)-2,3,4,5,9,10,11,11a-octahydro-1H,8bH-cyclopenta[b][1,4]diazocino[7,8,1-hi]indole; or
    (−)-(8bR*,11aR*)-2,3,4,5,9,10,11,11a-octahydro-1H,8bH-cyclopenta[b][1,4]diazocino[7,8,1-hi]indole;
    or a pharmaceutically acceptable salt thereof.

15. The compound of claim 1 selected from:
    a) 3-methyl-2,3,4,5,9,10,11,12-octahydro-1H-[1,4]diazocino[7,8,1-jk]carbazole;
    b) 2,3,4,5,9,10,11,12-octahydro-1H-[1,4]diazocino-1H-[7,8,1-jk]carbazole;
    c) 3-methyl-2,3,4,5,8b,9,10,11,12,12a-decahydro-1H[1,4]diazocino[7,8,1-jk]carbazole;
    d) 2,3,4,5,8b,9,10,11,12,12a-decahydro-1H-[1,4]diazocino[7,8,1-jk]carbazole;
    e) 6-chloro-3-methyl-2,3,4,5,9,10,11,12-octahydro-1H-[1,4]diazocino[7,8,1-jk]carbazole;
    f) 6-chloro-2,3,4,5,9,10,11,12-octahydro-1H-[1,4]diazocino[7,8,1-jk]carbazole;
    g) 6-chloro-3-ethyl-2,3,4,5,8b,9,10,11,12,12a-decahydro-1H-[1,4]diazocino[7,8,1-jk]carbazole;
    h) 8-fluoro-3-methyl-2,3,4,5,9,10,11,12-octahydro-1H-[1,4]diazocino[7,8,1-jk]carbazole;
    i) 8-fluoro-3-methyl-2,3,4,5,8b,9,10,11,12,12a-decahydro-1H-[1,4]diazocino[7,8,1-jk]carbazole;
    j) 8-fluoro-2,3,4,5,9,10,11,12-octahydro-1H-[1,4]diazocino[7,8,1-jk]carbazole;
    k) 8-fluoro-2,3,4,5,8b,9,10,11,12,12a-decahydro-1H[1,4]diazocino[7,8,1-jk]carbazole;
    l) 8-chloro-3-methyl-2,3,4,5,9,10,11,12-octahydro-1H-[1,4]diazocino[7,8,1-jk]carbazole;
    m) 8-chloro-3-methyl-2,3,4,5,8b,9,10,11,12,12a-decahydro-1H-[1,4]diazocino[7,8,1-jk]carbazole;
    n) 8-chloro-2,3,4,5,9,10,11,12-octahydro-1H-[1,4]diazocino[7,8,1-jk]carbazole; or
    o) 8-chloro-2,3,4,5,8b,9,10,11,12,12a-decahydro-1H-[1,4]diazocino[7,8,1-jk]carbazole;
    or a pharmaceutically acceptable salt thereof.

16. The compound of claim 15 selected from:
    (+)-(8bR*,12aR*)-8-fluoro-2,3,4,5,8b,9,10,11,12,12a-decahydro-1H-[1,4]diazocino[7,8,1-jk]carbazole;
    (−)-(8bR*,12aR*)-8-fluoro-2,3,4,5,8b,9,10,11,12,12a-decahydro-1H-[1,4]diazocino[7,8,1-jk]carbazole;
    (+)-(8bR*,12aR*)-8-chloro-2,3,4,5,8b,9,10,11,12,12a-decahydro-1H-[1,4]diazocino[7,8,1-jk]carbazole;
    (−)-(8bR*,12aR*)-8-chloro-2,3,4,5,8b,9,10,11,12,12a-decahydro-1H-[1,4]diazocino[7,8,1-jk]carbazole;
    (+)-(8bR*,12aR*)-2,3,4,5,8b,9,10,11,12,12a-decahydro-1H-[1,4]diazocino[7,8,1-jk]carbazole; or
    (−)-(8bR*,12aR*)-2,3,4,5,8b,9,10,11,12,12a-decahydro-1H-[1,4]diazocino[7,8,1-jk]carbazole;
    or a pharmaceutically acceptable salt thereof.

17. The compound of claim 1 selected from
    a) 3-methyl-2,3,4,5,10,11,12,13-octahydro-1H,9H-cyclohepta[b][1,4]diazocino[7,8,1-hi]indole;
    b) 2,3,4,5,10,11,12,13-octahydro-1H,9H-cyclohepta[b][1,4]diazocino[7,8,1-hi]indole;
    c) 6-chloro-3-methyl-2,3,4,5,10,11,12,13-octahydro-1H,9H-cyclohepta[b][1,4]diazocino[7,8,1-hi]indole;
    d) 6-chloro-3-methyl-2,3,4,5,9,10,11,12,13,13a-decahydro-1H,8bH-cyclohepta[b][1,4]diazocino[7,8,1-hi]indole;
    e) 6-chloro-2,3,4,5,10,11,12,13-octahydro-1H,9H-cyclohepta[b][1,4]diazocino[7,8,1-hi]indole; or
    f) 6-chloro-2,3,4,5,9,10,11,12,13,13a-decahydro-1H,8bH-cyclohepta[b][1,4]diazocino[7,8,1-hi]indole;
    or a pharmaceutically acceptable salt thereof.

18. The compound of claim 1 selected from:
    a) 3-methyl-2,3,4,5,11,12-hexahydro-1H,9H-[1,4]diazocino[7,8,1-hi]thiopyrano[4,3-b]indole; or
    b) 3-methyl-2,3,4,5,9,10,11,12-octahydro-1H,9H-[1,4]diazocino[7,8,1-hi]thiopyrano[4,3-b]indole;
    or a pharmaceutically acceptable salt thereof.

19. A method of treating a mammal suffering from a condition selected from schizophrenia, schizophreniform disorder, schizoaffective disorder, delusional disorder, or psychosis comprising providing to the mammal suffering from the condition, a therapeutically effective amount of at least one compound of Formula I:

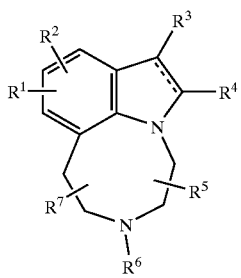

wherein
 R¹ and R² are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;
 R³ and R⁴ are, independently, hydrogen or alkyl of 1 to 6 carbon atoms, or R³ and R⁴, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sulfone, wherein the cyclic moiety may optionally be substituted with 1 to 3 alkyl moieties of 1 to 6 carbon atoms;
 R⁵, R⁶ and R⁷ are, independently, hydrogen or alkyl of 1 to 6 carbon atoms; and
 a dotted line represents an optional double bond;
or a pharmaceutically acceptable salt thereof.

20. The method of claim 19 wherein the condition is schizophrenia.

21. The method of claim 19 wherein the mammal is human.

22. A method of treating a mammal suffering from a condition selected from bipolar disorders, depressive disorders, major depressive episodes, mixed episodes, anxiety disorders, or adjustment disorders comprising providing to the mammal suffering from the condition, a therapeutically effective amount of at least one compound of Formula I:

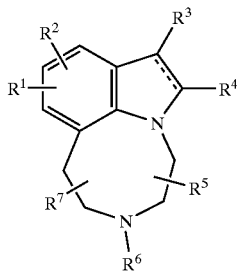

wherein
 R¹ and R² are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;
 R³ and R⁴ are, independently, hydrogen or alkyl of 1 to 6 carbon atoms, or R³ and R⁴, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sulfone, wherein the cyclic moiety may optionally be substituted with 1 to 3 alkyl moieties of 1 to 6 carbon atoms;
 R⁵, R⁶ and R⁷ are, independently, hydrogen or alkyl of 1 to 6 carbon atoms; and
 a dotted line represents an optional double bond;
or a pharmaceutically acceptable salt thereof.

23. The method of claim 22 wherein the bipolar disorder is bipolar I disorder, bipolar II disorder, or cyclothymic disorder; the depressive disorder is major depressive disorder, dysthymic disorder, or substance-induced mood disorder; the mood episode is major depressive episode, manic episode, mixed episode, or hypomanic episode; the anxiety disorder is panic attack, agoraphobia, panic disorder, specific phobia, social phobia, obsessive compulsive disorder, posttraumatic stress disorder, acute stress disorder, generalized anxiety disorder, separation anxiety disorder, or substance-induced anxiety disorder.

24. The method of claim 22 wherein the condition is depressive disorder or mood episode.

25. A method of treating a mammal suffering from a condition selected from epilepsy, sleep disorders, or sexual dysfunction comprising providing to the mammal suffering from the condition, a therapeutically effective amount of at least one compound of Formula I:

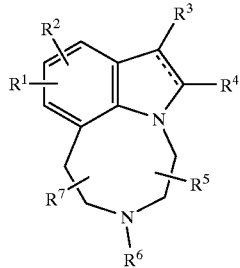

wherein
 R¹ and R² are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;
 R³ and R⁴ are, independently, hydrogen or alkyl of 1 to 6 carbon atoms, or R³ and R⁴, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sulfone, wherein the cyclic moiety may optionally be substituted with 1 to 3 alkyl moieties of 1 to 6 carbon atoms;

$R^5$, $R^6$ and $R^7$ are, independently, hydrogen or alkyl of 1 to 6 carbon atoms; and a dotted line represents an optional double bond;

or a pharmaceutically acceptable salt thereof.

26. The method of claim 25 wherein the mammal is a human.

27. A method of treating a mammal suffering from spinal cord injury comprising providing to the mammal suffering from the condition, a therapeutically effective amount of at least one compound of Formula I:

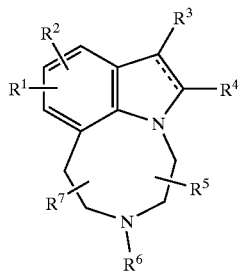

I wherein $R^1$ and $R^2$ are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

$R^3$ and $R^4$ are, independently, hydrogen or alkyl of 1 to 6 carbon atoms, or $R^3$ and $R^4$, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sulfone, wherein the cyclic moiety may optionally be substituted with 1 to 3 alkyl moieties of 1 to 6 carbon atoms;

$R^5$, $R^6$ and $R^7$ are, independently, hydrogen or alkyl of 1 to 6 carbon atoms; and a dotted line represents an optional double bond;

or a pharmaceutically acceptable salt thereof.

28. A pharmaceutical composition comprising a) at least one compound of Formula I

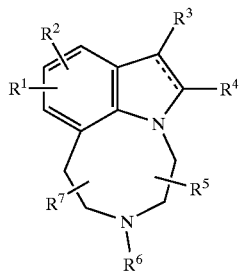

I wherein $R^1$ and $R^2$ are, independently, hydrogen, hydroxy, halo, cyano, carboxamido, carboalkoxy of two to six carbon atoms, trifluoromethyl, trifluoromethoxy, alkyl of 1 to 6 carbon atoms, alkoxy of 1 to 6 carbon atoms, alkanoyloxy of 2 to 6 carbon atoms, alkanoyl of 2 to 6 carbon atoms, amino, mono-or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

$R^3$ and $R^4$ are, independently, hydrogen or alkyl of 1 to 6 carbon atoms, or $R^3$ and $R^4$, taken together with the carbons to which they are attached, form a cyclic moiety selected from a cycloalkane of 5 to 8 carbon atoms, cycloalkene of 5 to 8 carbon atoms, bridged bicyclic alkane of 6 to 9 carbon atoms, bridged bicyclic alkene of 6 to 9 carbon atoms, pyran or thiopyran in which the sulfur atom is optionally oxidized to a sulfoxide or sulfone, wherein the cyclic moiety may optionally be substituted with 1 to 3 alkyl moieties of 1 to 6 carbon atoms;

$R^5$, $R^6$ and $R^7$ are, independently, hydrogen or alkyl of 1 to 6 carbon atoms; and a dotted line represents an optional double bond;

or a pharmaceutically acceptable salt thereof; and b) at least one pharmaceutically acceptable carrier or excipient.

29. The composition of claim 28 wherein $R^3$ and $R^4$ are taken together with the carbon atoms to which they are attached to form a cycloalkane of 5 to 8 carbon atoms optionally substituted with 1 to 3 alkyl moieties of 1 to 3 carbon atoms, cycloalkene of 5 to 8 carbon atoms, optionally substituted with 1 to 3 alkyl moieties of 1 to 3 carbon atoms, pyran or thiopyran, in which the sulfur atom is optionally oxidized to a sulfoxide or sulfone.

30. The composition of claim 28 wherein $R^1$ and $R^2$ are independently selected from hydrogen, halo, trifluoromethyl or alkyl of 1 to 3 carbon atoms; $R^5$, $R^6$ and $R^7$ are each hydrogen; and $R^3$ and $R^4$, taken together with the carbon atoms to which they are attached, form cyclopentane, cyclohexane or cyclohexene.

31. A method of treating a mammal suffering from obesity comprising providing to the mammal, a therapeutically effective amount of at least one compound of Formula I of claim 1.

32. A method of treating a mammal suffering from an eating disorder comprising providing to the mammal, a therapeutically effective amount of at least one compound of Formula I of claim 1.

* * * * *